US011432889B2

(12) United States Patent
Usuki et al.

(10) Patent No.: US 11,432,889 B2
(45) Date of Patent: Sep. 6, 2022

(54) ROBOTIC SURGICAL INSTRUMENT, METHOD OF ASSEMBLING THE SAME, AND ROBOTIC SURGICAL SYSTEM

(71) Applicant: MEDICAROID CORPORATION, Kobe (JP)

(72) Inventors: Yu Usuki, Kobe (JP); Kenji Ago, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 256 days.

(21) Appl. No.: 16/548,783

(22) Filed: Aug. 22, 2019

(65) Prior Publication Data

US 2020/0069380 A1    Mar. 5, 2020

(30) Foreign Application Priority Data

Aug. 28, 2018  (JP) .............................. JP2018-159338

(51) Int. Cl.
| | |
|---|---|
| *A61B 34/30* | (2016.01) |
| *A61B 17/29* | (2006.01) |
| *A61B 34/00* | (2016.01) |
| *A61B 17/00* | (2006.01) |

(52) U.S. Cl.
CPC .............. *A61B 34/30* (2016.02); *A61B 34/71* (2016.02); *A61B 2017/00477* (2013.01); *A61B 2017/00973* (2013.01); *A61B 2017/2902* (2013.01); *A61B 2017/2933* (2013.01); *A61B 2034/301* (2016.02); *A61B 2034/305* (2016.02)

(58) Field of Classification Search
CPC ......... A61B 34/30; A61B 34/71; A61B 34/37; A61B 2017/00477; A61B 2017/2933; A61B 2017/2927; A61B 2017/2948; A61B 2017/2932; A61B 2017/2939; A61B 2034/305; B25J 9/104
See application file for complete search history.

(56) References Cited

U.S. PATENT DOCUMENTS

| | | | | |
|---|---|---|---|---|
| 6,394,998 B1 * | 5/2002 | Wallace | ................. | A61B 34/71 606/1 |
| 8,382,790 B2 * | 2/2013 | Uenohara | .............. | A61B 17/29 606/205 |
| 2004/0266574 A1 | 12/2004 | Jinno et al. | | |
| 2008/0046122 A1 | 2/2008 | Manzo et al. | | |

(Continued)

FOREIGN PATENT DOCUMENTS

| | | |
|---|---|---|
| EP | 2470089 A1 | 7/2012 |
| WO | 2011/060042 A1 | 5/2011 |

*Primary Examiner* — Nathan J Jenness
(74) *Attorney, Agent, or Firm* — Metrolex IP Law Group, PLLC

(57) ABSTRACT

A robotic surgical instrument according to an embodiment may include: an end effector; a first support body that supports the end effector rotatably about a first shaft; a second support body that supports the first support body rotatably about a second shaft; an elongated element to rotate the first support body with respect to the second support body; and a shaft to which the second support body is connected. The elongated element includes a wire, an attachment fixed to the wire, and a protection tube fixed to the wire. The first support body includes a through-hole having a size in which the attachment and the protection tube are insertable.

17 Claims, 22 Drawing Sheets

(56) References Cited

U.S. PATENT DOCUMENTS

| | | | |
|---|---|---|---|
| 2010/0016852 A1* | 1/2010 | Manzo | A61B 18/1445 |
| | | | 606/46 |
| 2013/0144395 A1* | 6/2013 | Stefanchik | A61B 34/71 |
| | | | 623/20.11 |
| 2015/0209965 A1* | 7/2015 | Low | B25J 17/02 |
| | | | 294/200 |
| 2016/0051318 A1 | 2/2016 | Manzo et al. | |
| 2018/0311003 A1* | 11/2018 | Ishihara | A61B 34/35 |
| 2019/0216557 A1* | 7/2019 | Ishihara | A61B 34/71 |

\* cited by examiner

DIRECTION IN WHICH WIRE EXTENDS

ROBOTIC SURGICAL INSTRUMENT, METHOD OF ASSEMBLING THE SAME, AND ROBOTIC SURGICAL SYSTEM

CROSS REFERENCE TO RELATED APPLICATIONS

This application claims priority to Japanese Patent Application No. 2018-159338 filed on Aug. 28, 2018, the entire contents of which are incorporated herein by reference.

BACKGROUND

The disclosure relates to a robotic surgical instrument, a method of assembling the robotic surgical instrument, and a robotic surgical system. The disclosure may particularly relate to a robotic surgical instrument that includes a first support body supporting an end effector rotatably about a first shaft and a second support body supporting the first support body rotatably about a second shaft, a method of assembling the robotic surgical instrument, and a robotic surgical system.

In a related art, there has been known a robotic surgical instrument, which includes a first support body supporting an end effector rotatably about a first shaft and a second support body supporting the first support body rotatably about a second shaft, and a method of assembling such a robotic surgical instrument (e.g., see U.S. Pat. No. 6,394,998).

U.S. Pat. No. 6,394,998 discloses a surgical instrument that includes an end effector, a clevis (hereinafter, a first clevis) as a U-shaped coupling tool that supports the end effector pivotably about a pivot shaft (hereinafter, a first pivot shaft), and a clevis (hereinafter, a second clevis) that supports the first clevis pivotably about a pivot shaft (hereinafter, a second pivot shaft). The surgical instrument disclosed in U.S. Pat. No. 6,394,998 includes a first cable and a second cable that allow pivot of the first clevis with respect to the second clevis. In the first clevis, a cable passage is formed to extend along an axis direction of the first pivot shaft and allow the cables to pass therethrough.

The first cable and the second cable of the surgical instrument each include a thickened first end portion and a not-thickened second end portion.

When assembling the surgical instrument, the not-thickened second end portion of the first cable is inserted first through the cable passage, and the thickened first end portion is then fixed to a seat in the opposite side of the cable passage. By the same way as in inserting and fixing the first cable, the second cable is inserted from the opposite side of the cable passage so as to be fixed to the cable passage. Thereafter protection tubes are fixed to the first cable and the second cable.

In this way, the first cable and the second cable of the surgical instrument are engaged with the first clevis. Consequently, the first clevis pivots about an axis of the second pivot shaft by moving the first cable in a direction in which the first cable extends and moving the second cable in a direction in which the second cable extends.

SUMMARY

However, since the surgical instrument disclosed in U.S. Pat. No. 6,394,998 requires fixing of the protection tubes to the first cable and the second cable after inserting the two separated first and second cables through the cable passage, the assembly steps of the surgical instrument are complicated.

This may lead to a problem of the difficulty in improving the efficiency of assembly works of the surgical instrument.

An object of an embodiment of the disclosure is to provide a robotic surgical instrument, a method of assembling the robotic surgical instrument, and a robotic surgical system that can improve the efficiency of assembly works of the surgical instrument.

A first aspect of the disclosure may be a robotic surgical instrument. The robotic surgical instrument according to the first aspect may include: an end effector; a first support body that supports the end effector rotatably about a first shaft; a second support body that supports the first support body rotatably about a second shaft; an elongated element to rotate the first support body with respect to the second support body; and a shaft to which the second support body is connected. The elongated element includes a wire, an attachment fixed to the wire, and a protection tube fixed to the wire. The first support body includes a through-hole having a size in which the attachment and the protection tube are insertable.

A second aspect of the disclosure ma y be a robotic surgical system. The robotic surgical system according to the second aspect may include a robot arm; and a robotic surgical instrument that is detachably attached to the robot arm. The robotic surgical instrument may include: an end effector; a first support body that supports the end effector rotatably about a first shaft; a second support body that supports the first support body rotatably about a second shaft; an elongated element to rotate the first support body with respect to the second support body; a shaft to which the second support body is connected; and a housing that is to be attached to the robot arm. The elongated element includes a wire, an attachment fixed to the wire, and a protection tube fixed to the wire. The first support body includes a through-hole having a size in which the attachment and the protection tube are insertable.

A third aspect of the disclosure may be a method of assembling a robotic surgical instrument, which includes a first support body that supports an end effector rotatably about a first shaft, a second support body that supports the first support body rotatably about a second shaft, and an elongated element to rotate the first support body with respect to the second support body.

The method according to the third aspect may include: preparing the elongated element in which an attachment and a protection tube are fixed to a wire; and attaching the elongated element in which the attachment and the protection tube are fixed to the wire to the first support body by inserting the elongated element through a through-hole of the first support body having a size in which the attachment and the protection tube are insertable.

DETAILED DESCRIPTION

Figure 1:
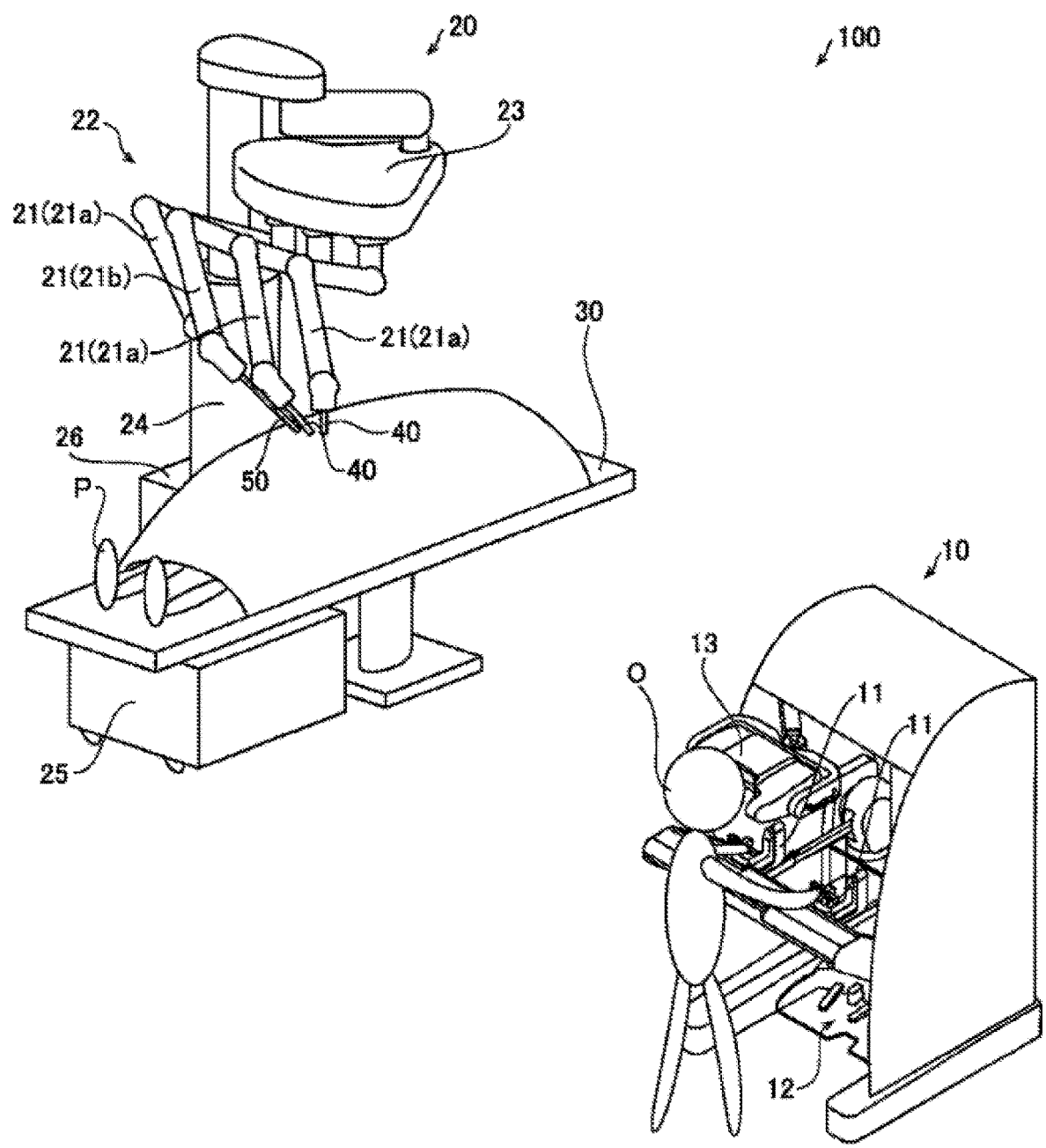
FIG. 1 is a diagram illustrating an overview of a robotic surgical system according to a first embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

First Embodiment (Configuration of Robotic Surgical System)

The configuration of a robotic surgical system 100 according to a first embodiment is described with reference to FIGS. 1 and 2.

As illustrated in FIG. 1, the robotic surgical system 100 includes a remote control apparatus 10 and a patient-side apparatus 20. The remote control apparatus 10 is provided to remotely control medical equipment provided for the patient-side apparatus 20. When an operator O, as a surgeon, inputs an action mode instruction to be executed by the patient-side apparatus 20, to the remote control apparatus 10, the remote control apparatus 10 transmits the action mode instruction to the patient-side apparatus 20 through a controller 26. In response to the action mode instruction transmitted from the remote control apparatus 10, the patient-side apparatus 20 operates medical equipment, including surgical instruments 40 and an endoscope 50, attached to robot arms 21. This allows minimally invasive surgery.

The patient-side apparatus 20 constitutes an interface to perform a surgery on a patient P. The patient-side apparatus 20 is positioned beside an operation table 30 on which the patient P is laid. The patient-side apparatus 20 includes robot arms 21. One of the robot arms 21 (21b) holds the endoscope 50 while the other robot arms 21 (21a) hold the surgical instruments 40. The robot arms 21 are commonly supported by a platform 23. Each of the robot arms 21 includes joints. Each joint includes a driver provided with a servo-motor and a position detector such as an encoder. The robot arms 21 are configured so that the medical equipment attached to each robot arm 21 is controlled by a driving signal given through the controller 26 and performs a desired movement.

The platform 23 is supported by a positioner 22 placed on the floor of an operation room. The positioner 22 includes a column 24 and a base 25. The column 24 includes an elevating shaft adjustable in the vertical direction. The base 25 includes wheels and is movable on the floor surface.

Figure 3:
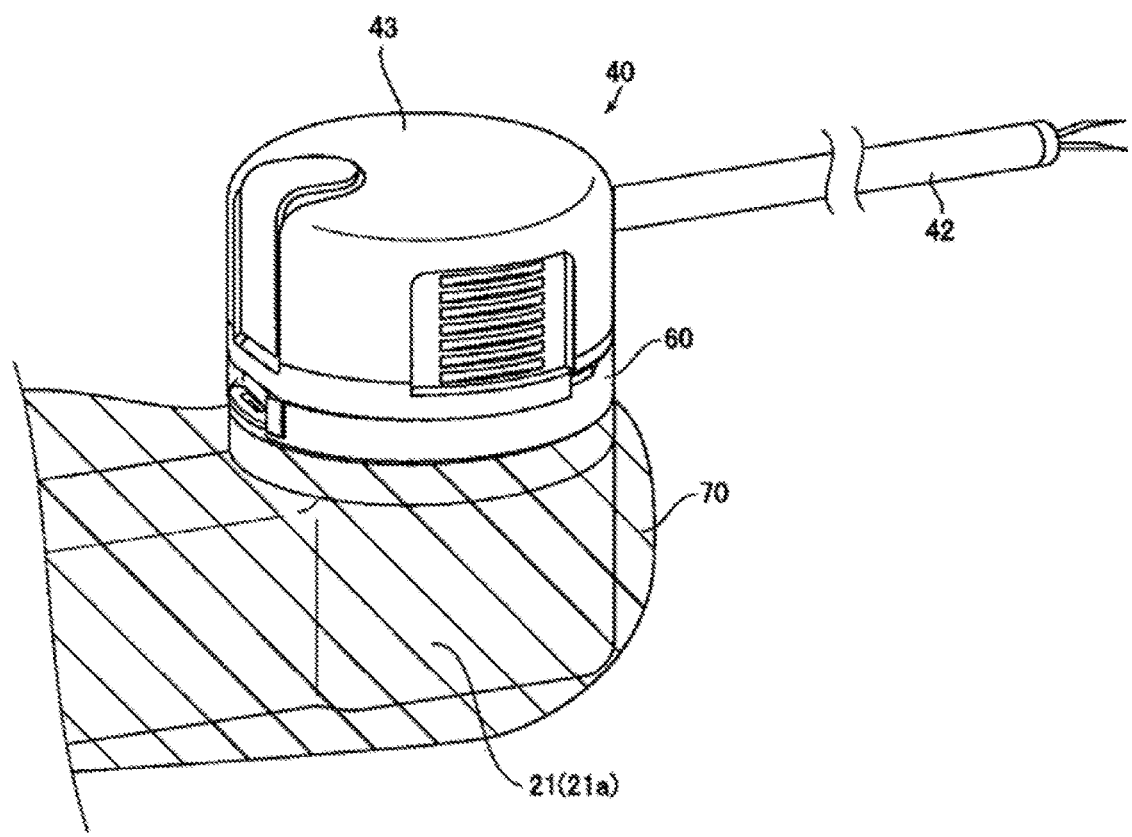
FIG. 3 is a diagram illustrating a perspective view of a state where a surgical instrument is attached to a robot arm through an adaptor according to a first embodiment.

The surgical instruments 40 as the medical equipment are detachably attached to the distal ends of the robot arms 21a. As illustrated in FIG. 3, each surgical instrument 40 includes: a housing 43, which is attached to the robot arm 21a; an elongated shaft 42; and an end effector 41, which is provided at the distal end portion of the shaft 42. The end effector 41 is grasping forceps, scissors, a hook, a high-frequency knife, a snare wire, a clamp, or a stapler, for example. The end effector 41 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effectors 41 of the surgical instruments 40 are then located near the surgery site.

To the distal end of the robot arm 21b, the endoscope 50 as the medical equipment is detachably attached. The endoscope 50 captures an image within the body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21b introduces the endoscope 50 into the body of the patient P through a trocar placed on the body surface of the patient P. The endoscope 50 is then located near the surgery site.

The remote control apparatus 10 constitutes the interface with the operator O. The remote control apparatus 10 is an apparatus that allows the operator O to operate medical equipment attached to the robot arms 21. Specifically, the remote control apparatus 10 is configured to transmit action mode instructions which are inputted by the operator O and are to be executed by the surgical instruments 40 and endoscope 50, to the patient-side apparatus 20 through the controller 26. The remote control apparatus 10 is installed beside the operation table 30 so that the operator O can see the condition of the patient P very well while operating the remote control apparatus 10, for example. The remote control apparatus 10 may be configured to transmit action mode instructions wirelessly and installed in a room different from the operation room where the operation table 30 is installed, for example.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object and include an action to supply current to a bipolar or monopolar instrument to burn off the surgery site.

The action modes to be executed by the endoscope 50 include the position and posture of the distal end portion of the endoscope 50 and setting of the zoom magnification, for example.

Figure 2:
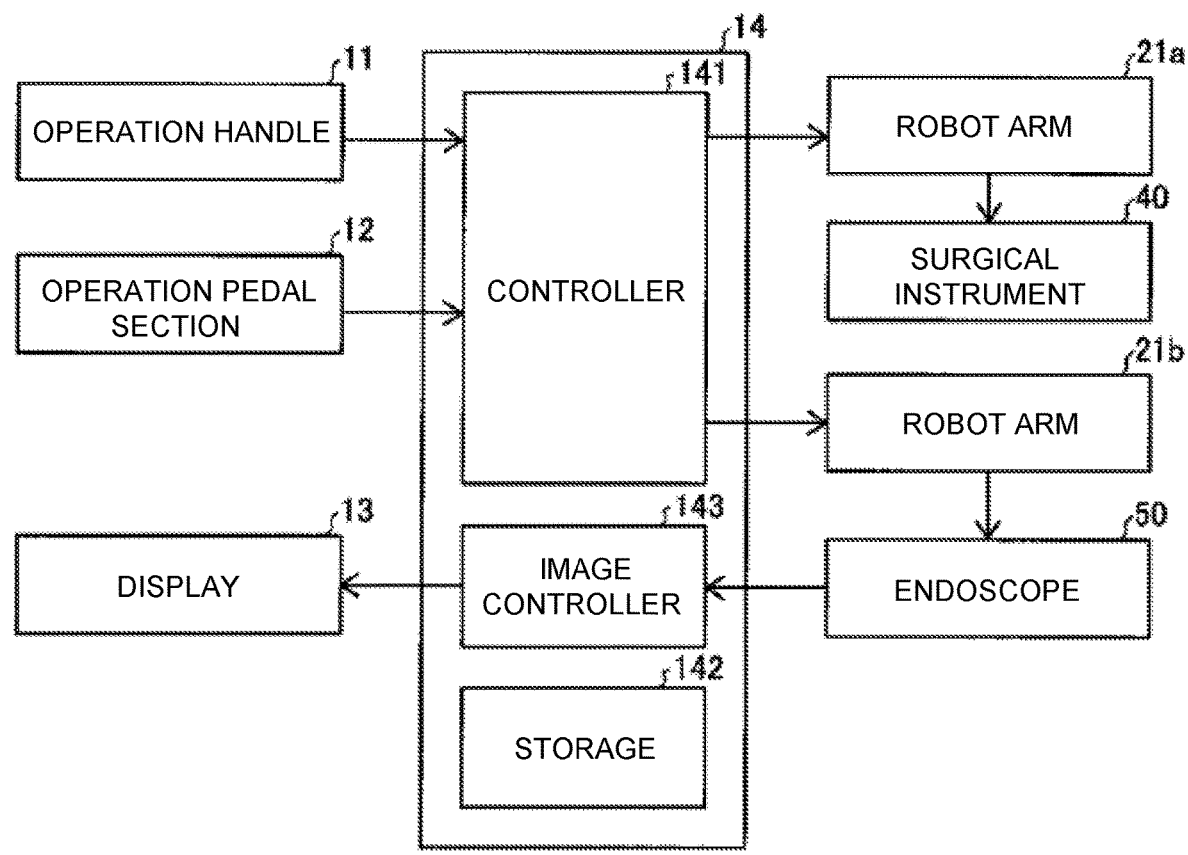
FIG. 2 is a block diagram illustrating a view of a control-related configuration of the robotic surgical system according to a first embodiment.

As illustrated in FIGS. 1 and 2, the remote control apparatus 10 includes operation handles 11, an operation pedal section 12, a display section 13, and a control apparatus 14.

The operation handles 11 are provided in order to remotely operate medical equipment attached to the robot arms 21. Specifically, the operation handles 11 accept operations by the operator O for operating medical equipment (the surgical instruments 40 and endoscope 50). The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 10 toward the front side. The operation handles 11 are configured to move in a predetermined three-dimensional operation region. Specifically, the operation handles 11 are configured so as to move up and down, right and left, and forward and rearward.

The remote control apparatus 10 and patient-side apparatus 20 constitute a master-slave system in terms of controlling movement of the robot arms 21a and robot arm 21b. The operation handles 11 constitute an operating section on the master side in the master-slave system, and the robot arms 21a and 21b holding medical equipment constitute an operating section on the slave side. When the operator O operates the operation handles 11, the movement of one of the robot arms 21a or 21b is controlled so that the distal end portion (the end effector 41 of the surgical instrument 40) of the robot arm 21a or the distal end portion (the endoscope 50) of the robot arm 21b moves following the movement of the operation handles 11.

The patient-side apparatus 20 controls the movement of the robot arms 21a in accordance with the set motion scaling ratio. When the motion scaling ratio is set to 1/2, for example, the end effectors 41 of the surgical instruments 40 move 1/2 of the movement distance of the operation handles 11. This allows precise fine surgery.

The operation pedal section 12 includes pedals to execute medical equipment-related functions. The pedals include a coagulation pedal, a cutting pedal, a camera pedal, and a clutch pedal. The pedals are operated by a foot of the operator O.

The coagulation pedal enables the surgical instrument 40 to coagulate a surgery site. Specifically, when the coagulation pedal is operated, voltage for coagulation is applied to the surgical instrument 40 to coagulate a surgery site. The cutting pedal enables the surgical instrument 40 to cut a surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. The position and orientation of the endoscope 50 are controllable by the operation handles 11 while the camera pedal is being pressed. The endoscope 50 is controlled by using both of the right and left operation handles 11, for example. Specifically, when the operator O rotates the right and left operation handles 11 about the middle point between the right and left operation handles 11, the endoscope 50 is rotated. When the operator O presses the right and left operation handles 11 together, the endoscope 50 goes forward into the body cavity. When the operator O pulls the right and left operation handles 11 together, the endoscope 50 goes back. When the operator O moves the right and left operation handles 11 together up, down, right, or left, the endoscope 50 moves up, down, right, or left, respectively.

The clutch pedal is used to temporarily disconnect operation-related connection between the operation handles 11 and the robot arms 21 to stop movement of the surgical instruments 40. Specifically, when the clutch pedal is being operated, the robot arms 21 of the patient-side apparatus 20 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21. The operator O restarts the operation for the operation handles 11 around the center thereof.

The display section 13 is configured to display images captured by the endoscope 50. The display section 13 includes a scope type display section or a non-scope type display section. The scope type display section is a display section that the operator O looks into. The non-scope type display section is a display section like an open-type display section that includes a flat screen and the operator O is able to see without looking into, such as normal displays for personal computers.

When the scope type display section is attached, the scope type display section displays 3D images captured by the endoscope 50 attached to the robot arm 21b of the patient-side apparatus 20. When the non-scope type display section is attached, the non-scope type display section also displays 3D images captured by the endoscope 50 provided for the patient-side apparatus 20. The non-scope type display section may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM and a RAM. The control apparatus 14 may be formed of a single controller performing centralized control or may be composed of controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display section 13. The image controller 143 performs processing and alternations for the images when needed.

(Configurations of Surgical Instrument)

With reference to FIGS. 3 to 16, the configuration of the surgical instrument 40 according to a first embodiment are described.

As illustrated in FIG. 3, the robot arm 21 is used in a clean area and is covered with a drape 70. In operation rooms, clean technique is used in order to prevent surgical incision sites and medical equipment from being contaminated by pathogen, foreign matters, or the like. The clean technique defines a clean area and a contaminated area, which is other than the clean area. The surgery sites are located in the clean area. Members of the surgical team, including the operator O, make sure that only sterile objects are placed in the clean area during surgery and perform sterilization for an object which is to be moved to the clean area from the contaminated area. Similarly, when the members of the surgical team including the operator O place their hands in the contaminated area, the members sterilize their hands before directly touching objects located in the clean area. Instruments used in the clean area are sterilized or are covered with sterile drapes 70. The surgical instrument 40 includes the housing 43, the elongated shaft 42, and the end effector 41. The housing 43 is attached to the robot arm 21a covered with the drape 70 through an adaptor 60. The shaft 42 is connected to the housing 43. The end effector 41 is provided at a tip or a distal end portion of the shaft 42.

Figure 4:
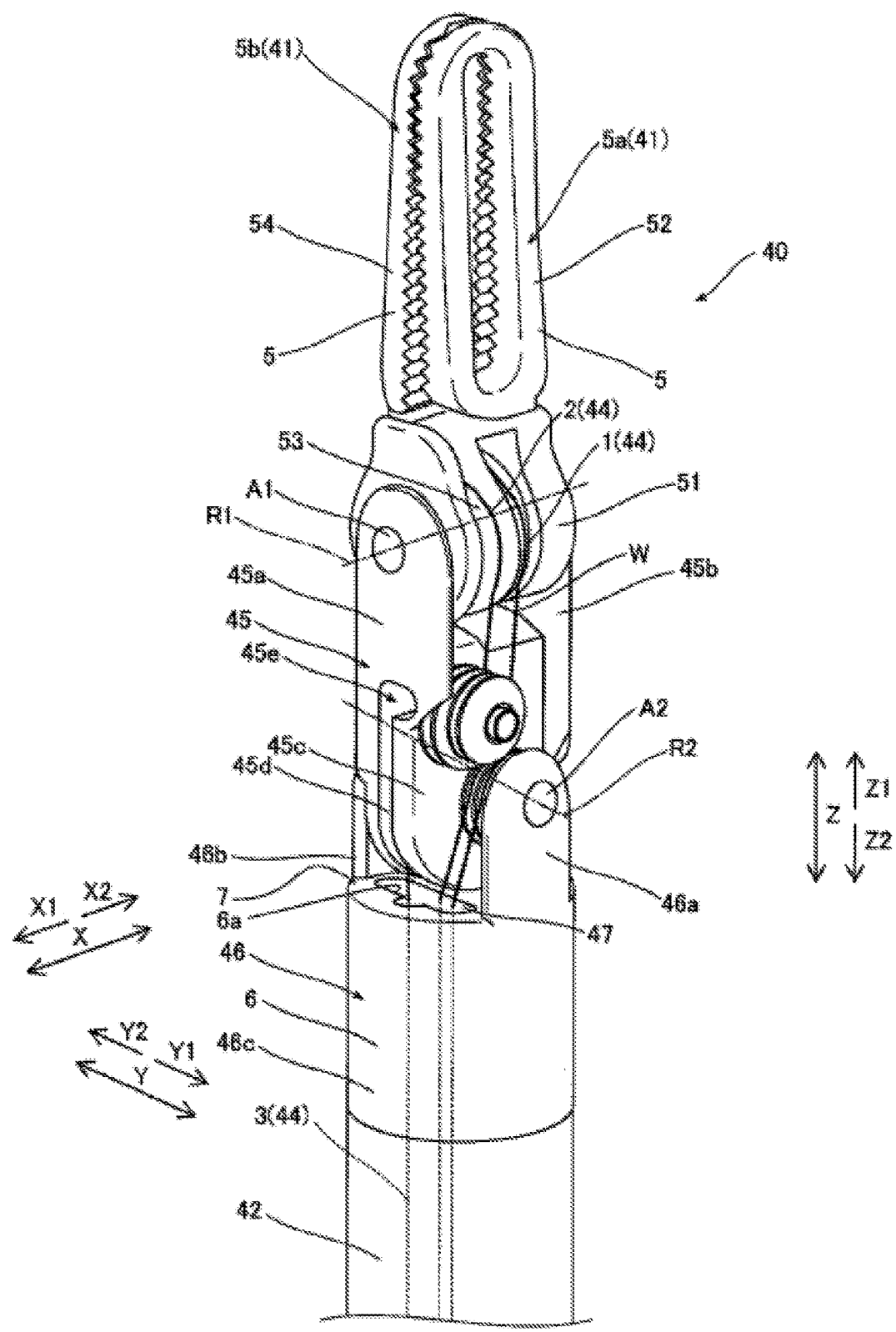
FIG. 4 is a diagram illustrating a perspective view of the surgical instrument according to a first embodiment.

As illustrated in FIG. 4, the surgical instrument 40 is configured to operate the end effector 41 at a tip or a distal end portion of surgical instrument 40 by driving of elongated elements 44 that are driven by a (not-illustrated) drive mechanism in the robot arm 21 (see FIG. 1). The surgical instrument 40 is an example of a robotic surgical instrument.

Specifically, the surgical instrument 40 includes the elongated elements 44, the above-described end effector 41, a first support body 45, a second support body 46, a silicone seal 47, and the shaft 42. The first support body 45 supports the end effector 41 rotatably about a first shaft A1. In other words, the end effector 41 is attached to the first support body 45 so as to rotate about a rotation axis R1 of the first shaft A1. The second support body 46 supports the first support body 45 rotatably about a second shaft A2. In other words, the first support body 45 is attached to the second support body 46 so as to rotate about a rotation axis R2 of the second shaft A2.

A direction in which the rotation axis R1 of the first shaft A1 extends is the X direction. One side of the X direction is the X1 direction and the other side is the X2 direction. A direction in which the rotation axis R2 of the second shaft A2 extends is the Y direction. One side of the Y direction is the Y1 direction and the other side is the Y2 direction. The X direction and the Y direction are orthogonal to each other. A direction orthogonal to the X and Y directions is the Z direction. One side of the Z direction is the Z1 direction and the other side is the Z2 direction.

Figure 5:
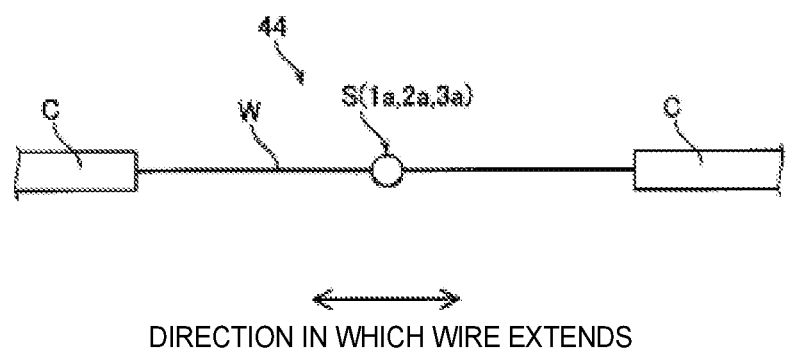
FIG. 5 is a diagram illustrating a schematic view of an elongated element of the surgical instrument according to a first embodiment.

As illustrated in FIG. 5, each elongated element 44 includes a wire W, an attachment S fixed to the wire W, and protection tubes C fixed to the wire W. The wire W is made of a metal such as stainless or tungsten. The protection tubes C are formed of rigid tubes partially covering the wire W. Plural (two) protection tubes C are arranged on the wire W. The attachment S is made of a metal such as stainless. The attachment S is formed in a shape protruding along a direction orthogonal to a direction in which the wire W extends. The attachment S is formed in a spherical shape or a column shape. The attachment S is arranged between the protection tubes C on the wire W.

As illustrated in FIG. 4, the end effector 41 is configured to perform procedures of the surgery site of the patient P based on the function of a type of the end effector 41. Specifically, the end effector 41 includes plural (two) end effector members 5. In other words, the end effector members 5 are a first jaw 5a and a second jaw 5b. The first jaw 5a and the second jaw 5b are attached to the first support body 45.

Figure 6:
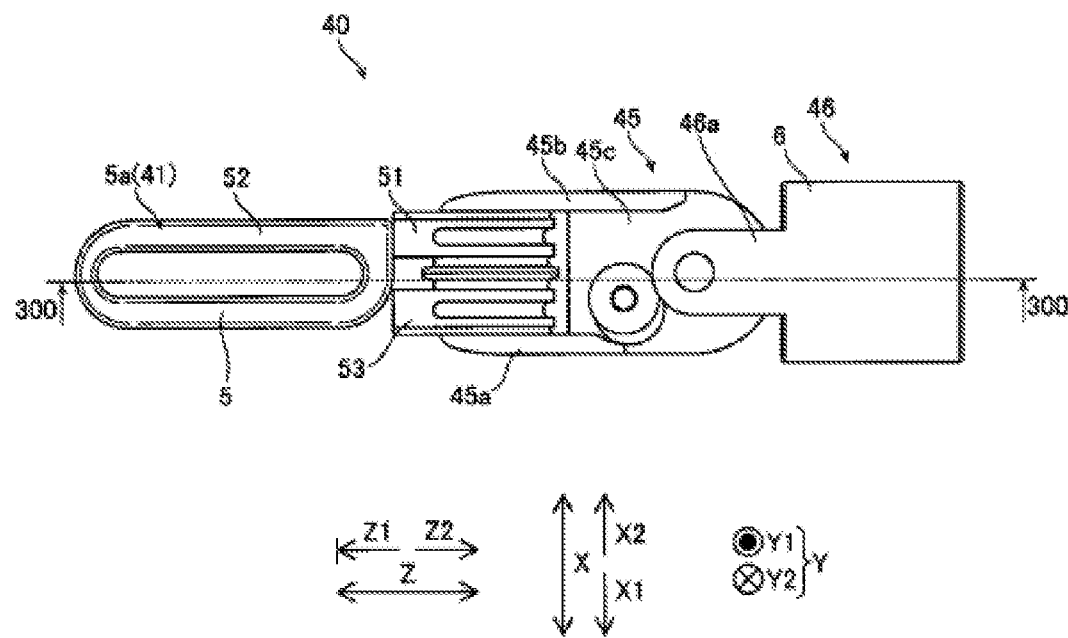
FIG. 6 is a diagram illustrating a side view of the surgical instrument as seen from the Y1 direction according to a first embodiment.
Figure 7A:
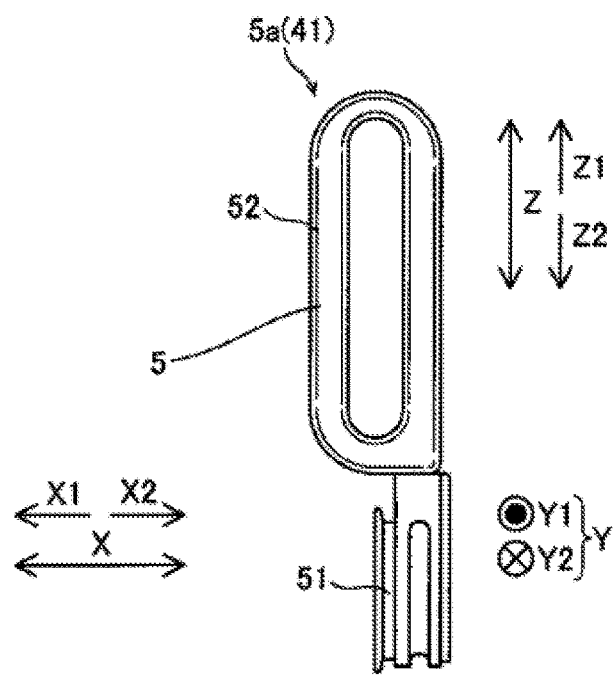
FIG. 7A is a diagram illustrating a schematic view of a first jaw.
Figure 7B:
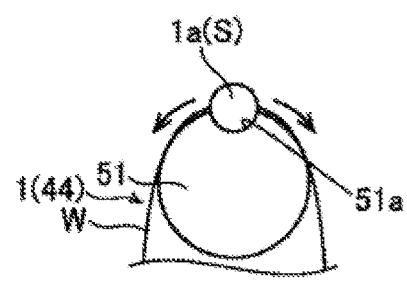
FIG. 7B is a diagram illustrating a schematic view of a first pulley section.
Figure 8A:
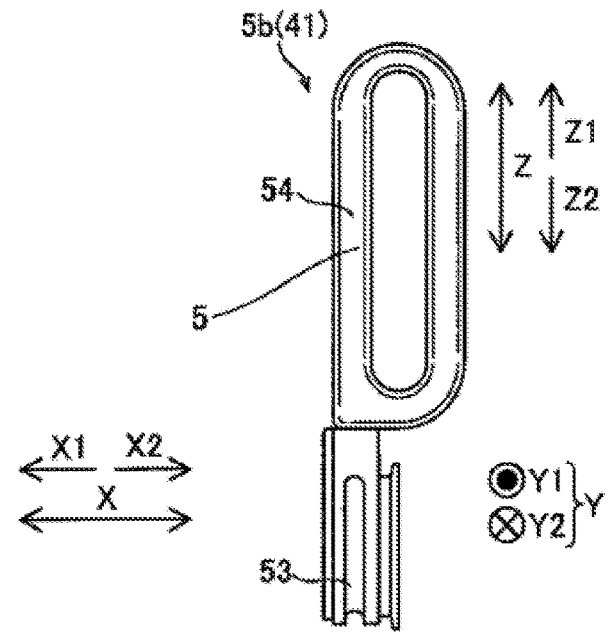
FIG. 8A is a diagram illustrating a schematic view of a second jaw.
Figure 8B:
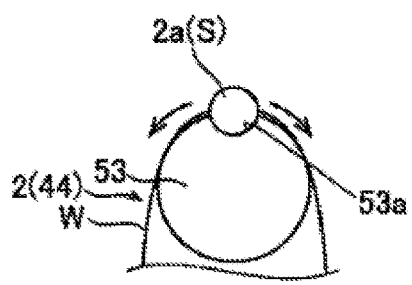
FIG. 8B is a diagram illustrating a schematic view of a second pulley section.

As illustrated in FIGS. 6, 7A, and 7B, the first jaw 5a includes a first pulley section 51 and a first procedure section 52. The first pulley section 51 forms a first recess 51a engaged with the attachment S of one of the elongated elements 44 (hereinafter, an attachment 1a of a first elongated element 1). The first procedure section 52 changes the orientation by rotation of the first pulley section 51 in accordance with movement of the first elongated element 1. The attachment 1a of the first elongated element 1 is formed in a column shape. As illustrated in FIGS. 6, 8A, and 8B, the second jaw 5b includes a second pulley section 53 and a second procedure section 54. The second pulley section 53 forms a second recess 53a engaged with the attachment S of one of the elongated elements 44 (hereinafter, an attachment 2a of a second elongated element 2). The second procedure section 54 changes the orientation by rotation of the second pulley section 53 in accordance with movement of the second elongated element 2. The attachment 2a of the second elongated element 2 is formed in a column shape.

(First Support Body)

Figure 9:
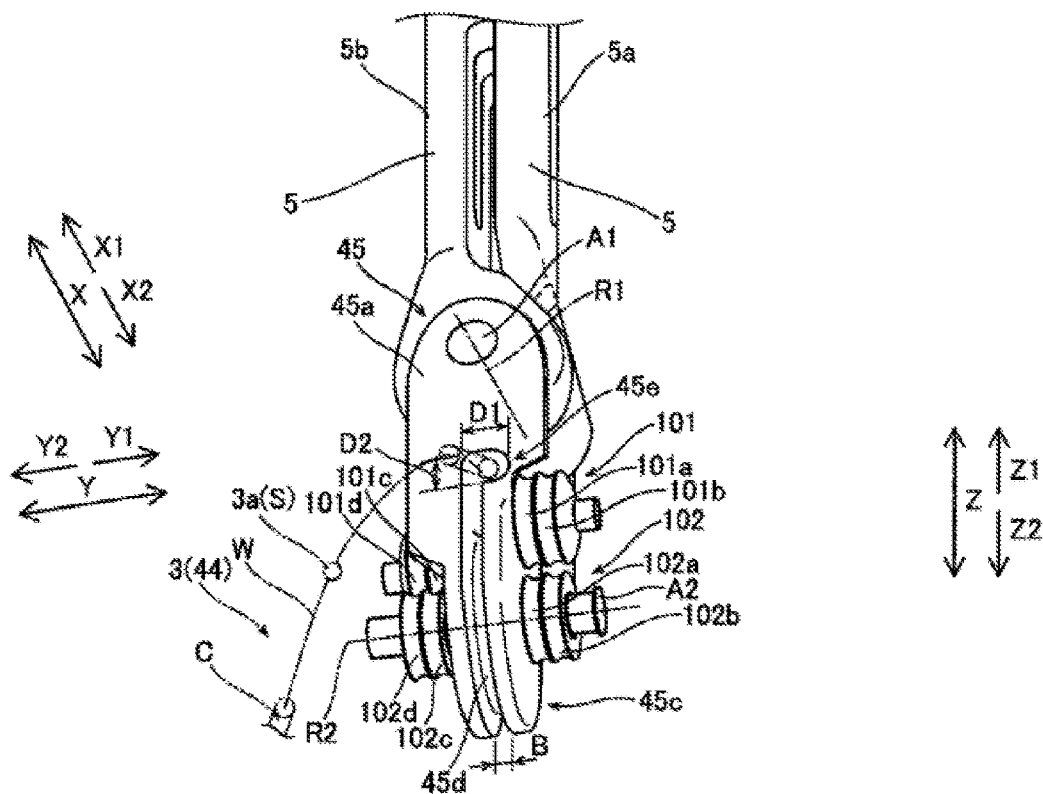
FIG. 9 is a diagram illustrating a perspective view of the surgical instrument from which a second support body is detached as seen from the X1 direction according to a first embodiment.
Figure 10:
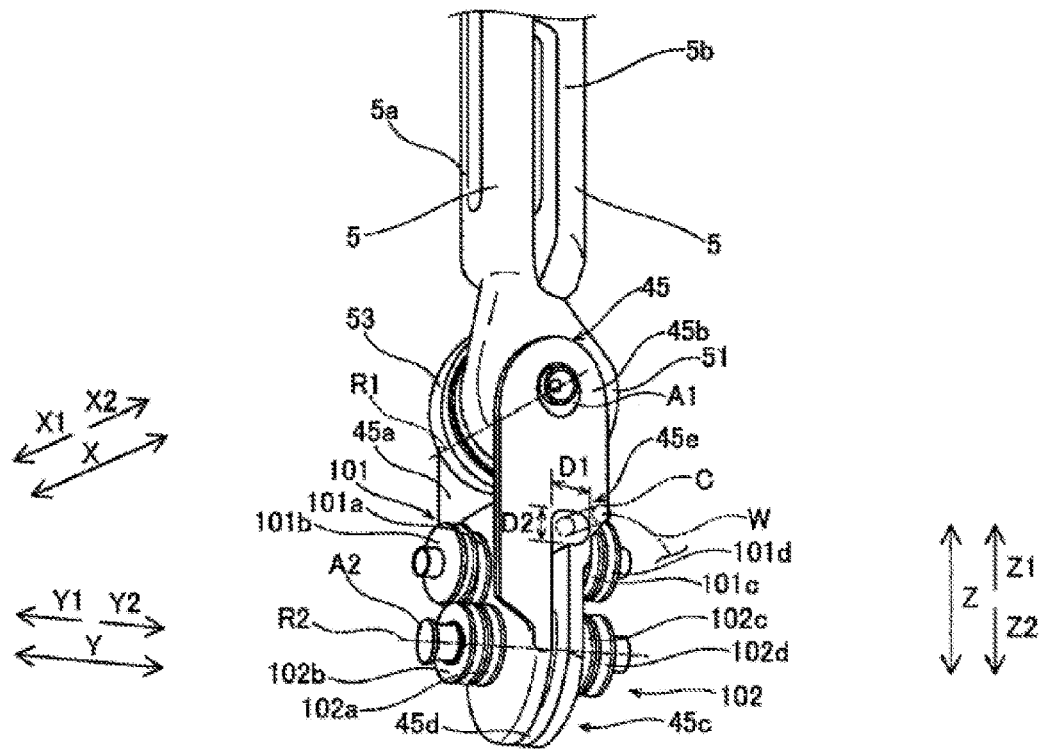
FIG. 10 is a diagram illustrating a perspective view of the surgical instrument from which the second support body is detached as seen from the X2 direction according to a first embodiment.

As illustrated in FIGS. 9 and 10, the first support body 45 includes a first protrusion section 45a, a second protrusion section 45b, and a third pulley section 45c. The first protrusion section 45a protrudes in the Z1 direction from an end portion on the X1 side of the third pulley section 45c. The first protrusion section 45a supports an end portion on the X1 side of the first shaft A1. The second protrusion section 45b protrudes in the Z1 direction from an end portion on the X2 side of the third pulley section 45c. The second protrusion section 45b supports an end portion on the X2 side of the first shaft A1. The third pulley section 45c is rotatably supported by the second shaft A2. The third pulley section 45c includes a pulley groove 45d formed along a circumferential direction of the second shaft A2. The third pulley section 45c is provided between the first protrusion section 45a and the second protrusion section 45b. The third pulley section 45c is arranged on the Z2 side of the first and second pulley sections 51 and 53. The third pulley section 45c is an example of a pulley section.

<Through-Hole>

The first support body 45 of a first embodiment includes a through-hole 45e having the size large enough to insert the attachment S and the protection tubes C. Specifically, the through-hole 45e is formed to allow insertion therethrough of one of the elongated elements 44 (hereinafter, a third elongated element 3) in which the attachment S and the protection tubes C are fixed to the wire W. The attachment S of the third elongated element 3 is an attachment 3a of the third elongated element 3.

Since the third elongated element 3 in which the attachment 3a of the third elongated element 3 and the protection tubes C are fixed to the wire W can be directly inserted through the through-hole 45e, it is easy to attach the third elongated element 3 in which the attachment S and the protection tubes C are fixed to the wire W to the first support body 45. Consequently, the efficiency of assembly works of the surgical instrument 40 can be more improved than a case of fixing the attachment 3a and the protection tubes C of the third elongated element 3 after inserting the wire W through the through-hole 45e.

The through-hole 45e has a predetermined width D1 in the Y direction and a predetermined height D2 in the Z direction. The predetermined width D1 of the through-hole 45e is greater than a width B in the Y direction of the pulley groove 45d of the third pulley section 45c. This clearly shows the difference between the through-hole 45e and the pulley groove 45d of the third pulley section 45c, and thus it is easy to visually recognize the position for inserting the third elongated element 3 (the position of the through-hole 45e).

The predetermined width D1 of the through-hole 45e is smaller than the maximum width in the Y direction of the third pulley section 45c. The predetermined height D2 of the through-hole 45e is greater than lengths of the protection tubes C and the attachment S in a direction orthogonal to the direction in which the wire W of the third elongated element 3 extends (see FIG. 5). The predetermined height D2 of the through-hole 45e is smaller than a length in the Z direction of the first shaft A1. The through-hole 45e is formed in an oval shape that is long in the Y direction as seen from the X1 direction. Specifically, the predetermined width D1 is greater than the predetermined height D2 in the through-hole 45e.

As illustrated in FIGS. 9 and 10, the through-hole 45e is formed to linearly pass through the first support body 45 along the X direction. Specifically, the through-hole 45e is formed in an end portion on the Z1 side of the third pulley section 45c. The through-hole 45e is connected to a section on the Z1 side of the pulley groove 45d of the third pulley section 45c. The through-hole 45e has a predetermined length D3 (see FIG. 13) in the X direction. The predetermined length D3 (see FIG. 13) of the through-hole 45e is substantially equal to the maximum length in the X direction of the third pulley section 45c.

<Engagement Section>

Figure 11:
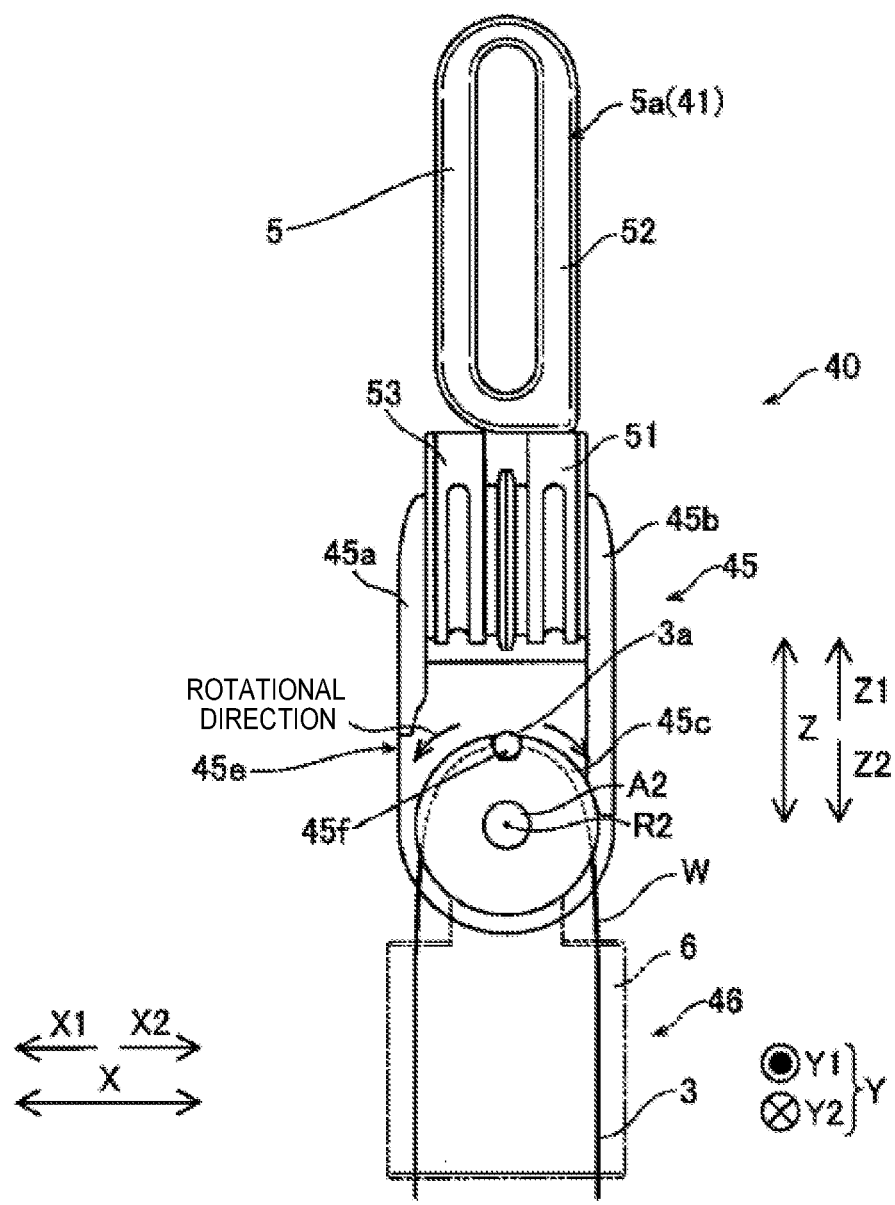
FIG. 11 is a diagram illustrating a side view of the surgical instrument in which parts of the second support body and a first support body are transparent as seen from the Y1 direction according to a first embodiment.

As illustrated in FIG. 11, the first support body 45 includes an engagement section 45f that is provided in the third pulley section 45c and engaged with the attachment 3a of the third elongated element 3 inserted in the through-hole 45e. When the wire W of the third elongated element 3 is drawn in the extending direction of the wire W and the attachment 3a of the third elongated element 3 is moved, the third pulley section 45c can be moved with the attachment 3a of the third elongated element 3. Consequently, the configuration for rotating the first support body 45 can be simplified.

The engagement section 45f is configured to be engaged with the attachment 3a of the third elongated element 3 to allow rotation of the third pulley section 45c about the rotation axis R2 of the second shaft A2 with the movement of the third elongated element 3. In other words, the third elongated element 3 is configured to rotate and drive the first support body 45 with respect to the second support body 46.

Figure 12:
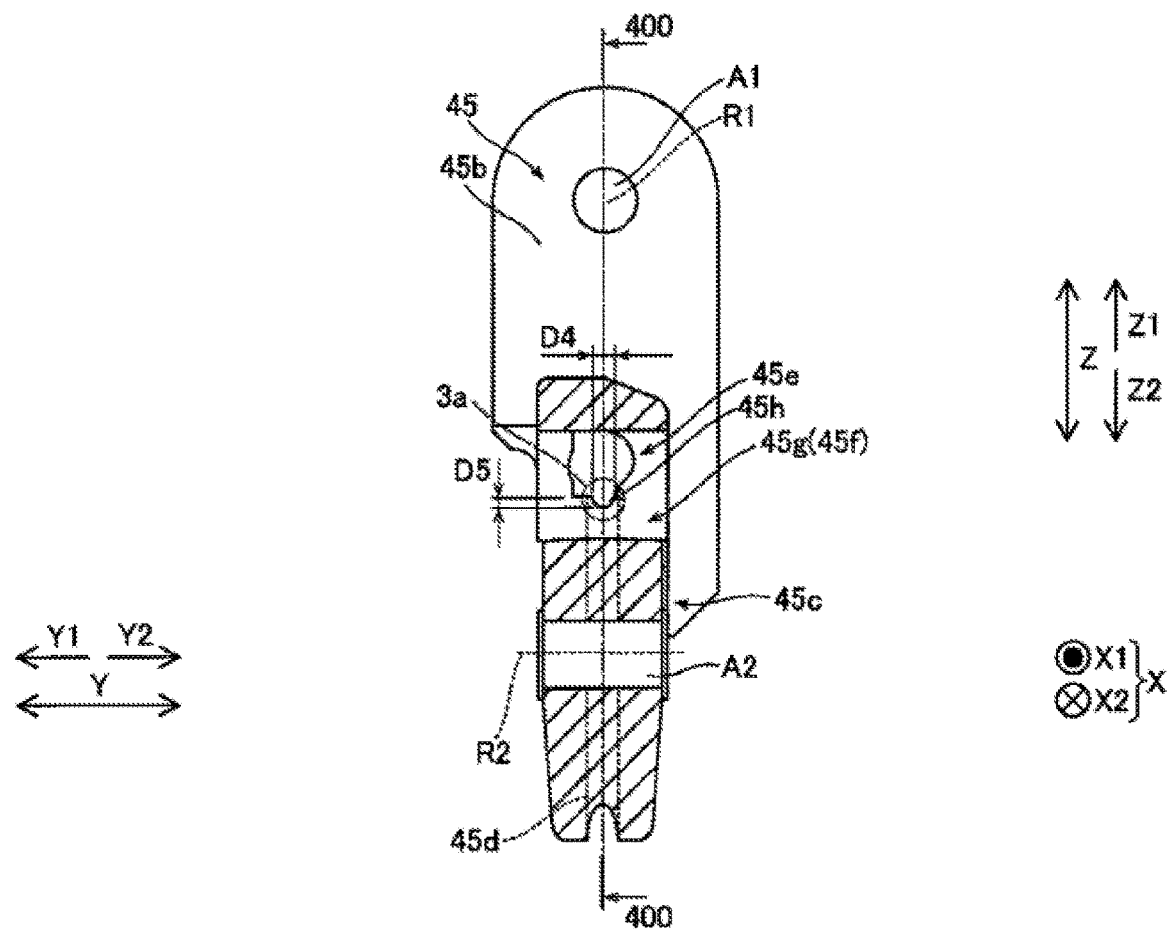
FIG. 12 is a diagram illustrating a cross-sectional view taken along the 300-300 line in FIG. 6.
Figure 13:
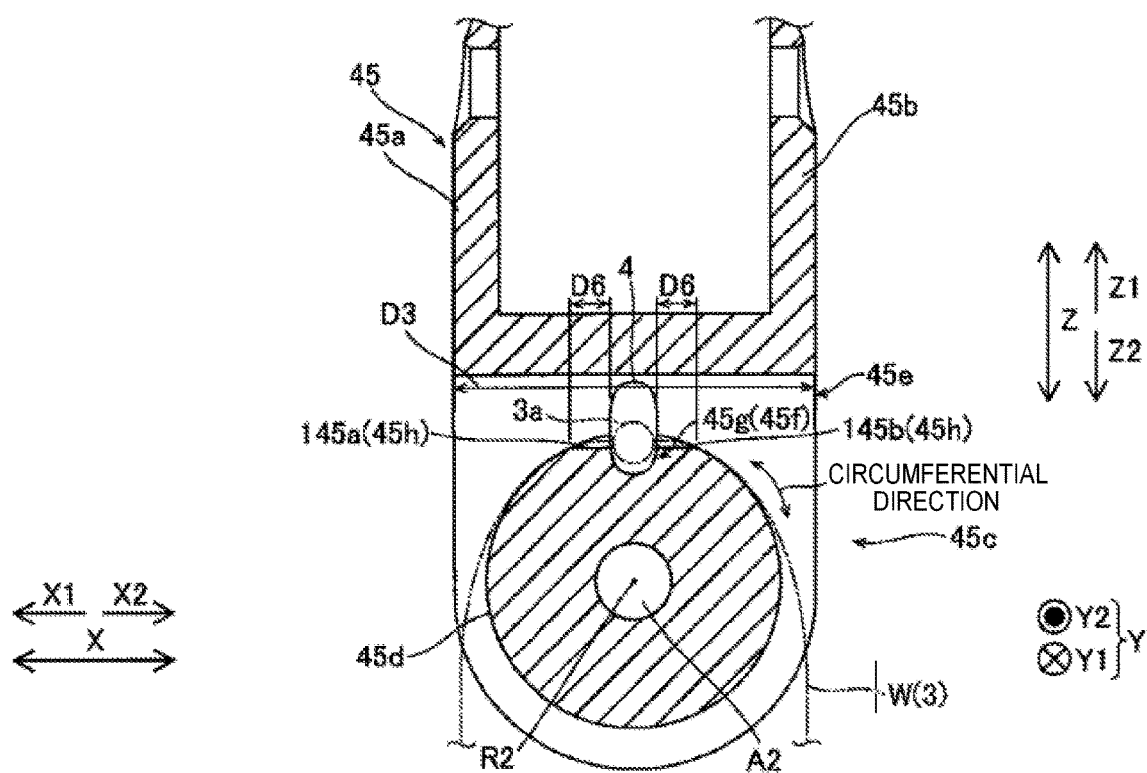
FIG. 13 is a diagram illustrating a cross-sectional view taken along the 400-400 line in FIG. 12.

Specifically, as illustrated in FIGS. 12 and 13, the engagement section 45f includes a third recess 45g to which the attachment 3a of the third elongated element 3 is fitted. It is possible to attach the third elongated element 3 to the first support body 45 by only fitting the attachment S to the third recess 45g of the engagement section 45f while the third elongated element 3 is inserted through the through-hole 45e. Consequently, the efficiency of assembly works of the surgical instrument 40 can be further improved.

The attachment 3a of the third elongated element 3 is formed in a spherical shape. The third recess 45g of the engagement section 45f is formed in a shape along the attachment 3a of the third elongated element 3. Specifically, the third recess 45g of the engagement section 45f is formed in a substantially semicircular shape as seen from the Y direction. For example, the third recess 45g may be formed in a semispherical shape or a semi-column shape. Since the shape of the third recess 45g of the engagement section 45f is formed in a shape along the outer shape of the attachment 3a of the third elongated element 3, the attachment 3a of the third elongated element 3 can be engaged with the third recess 45g of the engagement section 45f with no backlash. Consequently, the first support body 45 can be further accurately rotated using the third elongated element 3.

The third recess 45g of the engagement section 45f is a part of a through-hole 4 passing through the third pulley section 45c in the Y direction. The through-hole 4 is formed in an oval shape that is long in the Z direction as seen from the Y2 direction to connect the through-hole 45e and the third recess 45g so as to function as a communication passage that connects the through-hole 45e and the third recess 45g.

The through-hole 45e is formed so as to linearly extend along the X direction and be connected to the third recess 45g of the engagement section 45f via the through-hole 4. Specifically, the third recess 45g is a recess in the Z2 direction on a bottom surface of the section on the Z1 side of the pulley groove 45d of the third pulley section 45c. The third recess 45g is located in a position of the center portion in the Y direction of the through-hole 45e. The linear protection tubes C along the direction in which the wire W of the third elongated element 3 extends can be easily inserted through the through-hole 45e, and the attachment S can be directly engaged with the third recess 45g of the engagement section 45f by inserting the third elongated element 3 through the through-hole 45e. Consequently, the efficiency of assembly works of the surgical instrument 40 can be further improved.

<Wire Groove Section>

As illustrated in FIG. 12, the third pulley section 45c includes a wire groove section 45h, which is a recess in the Z2 direction on a bottom surface of an end portion on the Z1 side of the pulley groove 45d of the third pulley section 45c. As the wire W of the third elongated element 3 is inserted into the wire groove section 45h, easy positioning of the attachment 3a of the third elongated element 3 when attaching the third elongated element 3 to the first support body 45 can be made. Consequently, the attachment 3a of the third elongated element 3 can be fitted to an accurate position of the third recess 45g.

The wire groove section 45h is configured such that the wire W is fitted thereto when the attachment 3a of the third elongated element 3 is engaged with the engagement section 45f. Specifically, the wire groove section 45h has a predetermined width D4 in the Y direction and a predetermined depth D5 in the Z direction.

The predetermined width D4 of the wire groove section 45h is smaller than a width in the Y direction of the pulley groove 45d of the third pulley section 45c. This makes it possible to suppress displacement of the position of the attachment 3a of the third elongated element 3 in the Y direction when attaching the third elongated element 3 to the first support body 45 more than a case where the width in the Y direction of the wire groove section 45h is greater than the width B (see FIG. 9) in the Y direction of the pulley groove 45d of the third pulley section 45c. Consequently, the attachment 3a of the third elongated element 3 can be fitted to a further accurate position of the third recess 45g.

The predetermined depth D5 of the wire groove section 45h is greater than the diameter of the wire W. This makes positioning of the attachment 3a of the third elongated element 3 when attaching the third elongated element 3 to the first support body 45 easier than a case where the depth of the wire groove section 45h is smaller than the diameter of the wire W. Consequently, the attachment 3a of the third elongated element 3 can be reliably fitted to an accurate position of the third recess 45g.

The center position in the Y direction of the wire groove section 45h is located so as to substantially coincide with the center position in the Y direction of the pulley groove 45d of the third pulley section 45c.

An end portion on the Z1 side of the wire groove section 45h is provided to continue to the through-hole 45e. Specifically, the wire groove section 45h is connected to the through-hole 45e in the Z direction.

As illustrated in FIG. 13, the wire groove section 45h is configured to guide the wire W in the circumferential direction of the pulley groove 45d of the third pulley section 45c when the attachment 3a of the third elongated element 3 is engaged with the engagement section 45f. Specifically, the wire groove section 45h has a predetermined length D6 in the X direction. The wire groove section 45h is provided in sections adjacent to the third recess 45g in the circumferential direction and extends along the X direction. As the wire W of the third elongated element 3 is inserted into the wire groove section 45h, easy positioning of the attachment 3a of the third elongated element 3 when attaching the third elongated element 3 to the first support body 45 can be made. Consequently, the attachment 3a of the third elongated element 3 can be fitted to an accurate position of the third recess 45g.

The wire groove section 45h includes a first groove section 145a provided on the X1 side and a second groove section 145b provided on the X2 side. The first groove section 145*a* and the second groove section 145*b* each have the predetermined length D6 in the X direction.

An end portion on the X1 side of the first groove section 145*a* is provided to continue to the pulley groove 45*d* of the third pulley section 45*c*. Specifically, the first groove section 145*a* is connected to the pulley groove 45*d* of the third pulley section 45*c* in the circumferential direction. An end portion on the X2 side of the first groove section 145*a* is provided to continue to the third recess 45*g* of the engagement section 45*f*. Specifically, the first groove section 145*a* is connected to the third recess 45*g* of the engagement section 45*f* in the circumferential direction. An end portion on the X1 side of the second groove section 145*b* is provided to continue to the third recess 45*g* of the engagement section 45*f*. Specifically, the second groove section 145*b* is connected to the third recess 45*g* of the engagement section 45*f* in the circumferential direction. An end portion on the X2 side of the second groove section 145*b* is provided to continue to the pulley groove 45*d* of the third pulley section 45*c*. Specifically, the second groove section 145*b* is connected to the pulley groove 45*d* of the third pulley section 45*c* in the circumferential direction.

As illustrated in FIGS. 9 and 10, the first support body 45 includes a first pulley group 101 and a second pulley group 102 that guide the first elongated element 1 engaged with the first pulley section 51 and the second elongated element 2 engaged with the second pulley section 53. The first pulley group 101 is arranged on the Z1 side of the second shaft A2. The second pulley group 102 is arranged on the second shaft A2.

The first pulley group 101 includes a first inner pulley section 101*a* and a first outer pulley section 101*b*. The first inner pulley section 101*a* is adjacent to the Y1 side of the third pulley section 45*c*. The first outer pulley section 101*b* is adjacent to the Y1 side of the first inner pulley section 101*a*. The first pulley group 101 also includes a first inner pulley section 101*c* and a first outer pulley section 101*d*. The first inner pulley section 101*c* is adjacent to the Y2 side of the third pulley section 45*c*. The first outer pulley section 101*d* is adjacent to the Y2 side of the first inner pulley section 101*c*.

The second pulley group 102 includes a second inner pulley section 102*a* and a second outer pulley section 102*b*. The second inner pulley section 102*a* is adjacent to the Y1 side of the third pulley section 45*c*. The second outer pulley section 102*b* is adjacent to the Y1 side of the second inner pulley section 102*a*. The second pulley group 102 also includes a second inner pulley section 102*c* and a second outer pulley section 102*d*. The second inner pulley section 102*c* is adjacent to the Y2 side of the third pulley section 45*c*. The second outer pulley section 102*d* is adjacent to the Y2 side of the second inner pulley section 102*c*.

(Second Support Body)

Figure 14:
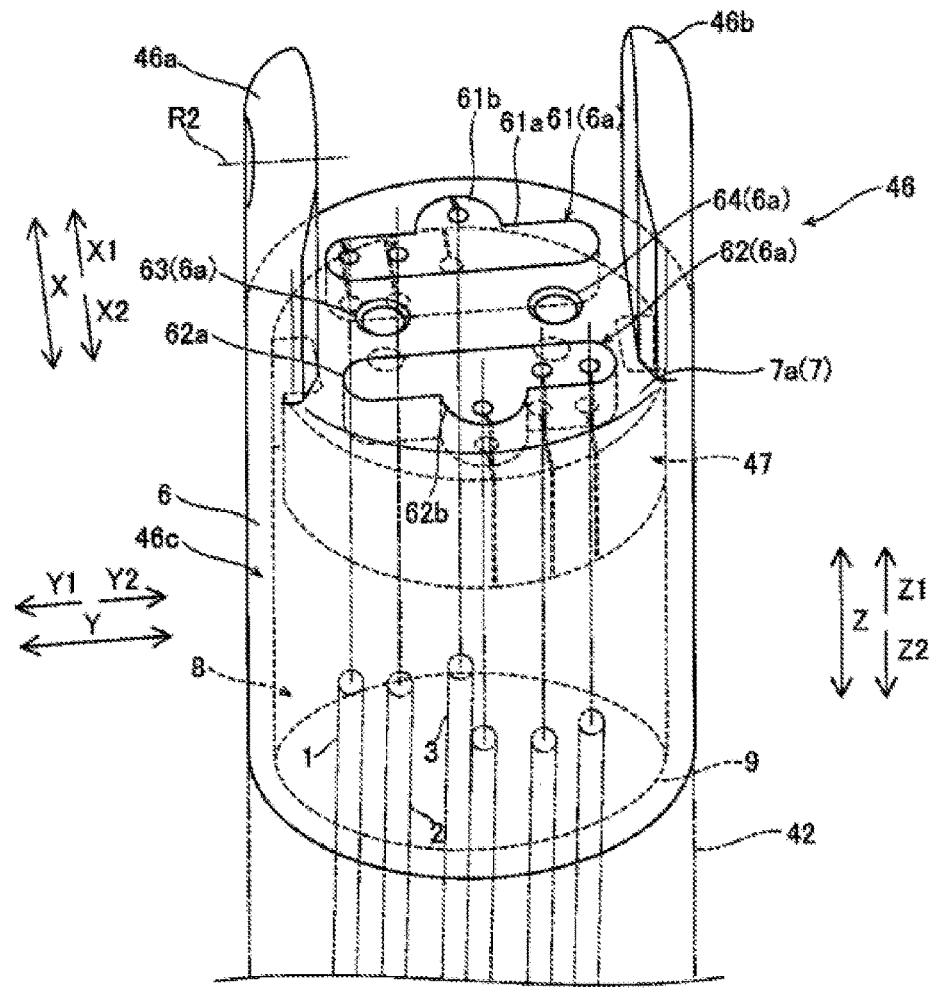
FIG. 14 is a diagram illustrating a perspective view of the second support body of the surgical instrument according to a first embodiment.

As illustrated in FIG. 14, the second support body 46 includes a connection base section 46*c*, a third protrusion section 46*a*, and a fourth protrusion section 46*b*. The connection base section 46*c* is connected to the shaft 42. The third protrusion section 46*a* and the fourth protrusion section 46*b* protrude from an end surface 7 on a side (the Z1 side) of the connection base section 46*c* in a direction in which the shaft 42 extends. The third protrusion section 46*a* protrudes in the Z1 direction from an end portion on the Y1 side of the connection base section 46*c*. The third protrusion section 46*a* supports an end portion on the Y1 side of the second shaft A2 (see FIG. 4). The fourth protrusion section 46*b* protrudes in the Z1 direction from an end portion on the Y2 side of the connection base section 46*c*. The fourth protrusion section 46*b* supports an end portion on the Y2 side of the second shaft A2 (see FIG. 4). An end portion on the Z2 side of the connection base section 46*c* is connected to an end portion on the Z1 side of the shaft 42. Specifically, the second support body 46 connects the first support body 45, which is supported by the third protrusion section 46*a* and the fourth protrusion section 46*b*, to the shaft 42 through the connection base section 46*c*. The third protrusion section 46*a* and the fourth protrusion section 46*b* are configured to rotatably support the first support body 45.

The connection base section 46*c* is formed in a substantially cylindrical shape. The connection base section 46*c* includes a side surface 6 and the end surface 7. The side surface 6 is provided along a circumferential direction around an axis extending in the Z direction. The end surface 7 is provided in an end portion of the side surface 6 on the other side opposite to the shaft 42 side (an end portion on the Z1 side). The connection base section 46*c* includes an inner space 8 surrounded by the side surface 6 and the end surface 7. The inner space 8 of the connection base section 46*c* is opened in the Z2 direction. Specifically, an end portion 9 on the Z2 side of the connection base section 46*c* is an opening that is opened in the Z2 direction. The end surface 7 is an example of a first end portion. The end portion 9 is an example of a second end portion.

The connection base section 46*c* is formed such that the later-described connection section 42*a* (see FIG. 16) of the shaft 42 is inserted into the connection base section 46*c* from the end portion 9 opposed to the end surface 7 in the extending direction of the shaft 42 (the Z1 direction). The end surface 7 includes a partition 7*a* including communication holes 6*a* passing through the end surface 7 in the extending direction of the shaft 42 (the Z direction). Specifically, the second support body 46 includes the communication holes 6*a* that pass through the partition 7*a* opposed to the shaft 42 in the extending direction of the shaft 42 (the Z direction). The partition 7*a* is configured to separate the inner space 8 and the outer space of the connection base section 46*c*.

The shaft 42 can be easily connected to the connection base section 46*c* only by inserting the connection section 42*a* (see FIG. 16) of the shaft 42 into the inner space 8 of the connection base section 46*c* through the end portion 9. Consequently, the efficiency of assembly works of the surgical instrument 40 can be further improved.

The communication holes 6*a* allow communication between the inner space 8 of the connection base section 46*c* and the outer space of the connection base section 46*c*. In the partition 7*a*, a communication hole 6*a* located on the X1 side (hereinafter, a first communication hole 61) and a communication hole 6*a* located on the X2 side (hereinafter, a second communication hole 62) are formed.

The first communication hole 61 and the second communication hole 62 are formed in a substantial T-shape as seen from the Z1 direction. The first communication hole 61 and the second communication hole 62 are formed line-symmetric with respect to an axis direction along the Y direction. The first communication hole 61 includes a first long hole 61*a* and a first dent 61*b*. The first long hole 61*a* extends in the Y direction. The first dent 61*b* protrudes in the X1 direction from a substantial center section in the Y direction of the first long hole 61*a*. The second communication hole 62 includes a second long hole 62*a* and a second dent 62*b*. The second long hole 62*a* extends in the Y direction. The second dent 62*b* protrudes in the X2 direction from a substantial center section in the Y direction of the second long hole 62*a*.

In the partition 7a, a communication hole 6a located on the Y1 side (hereinafter, a third communication hole 63) and a communication hole 6a located on the Y2 side (hereinafter, a fourth communication hole 64) are formed. The third communication hole 63 and the fourth communication hole 64 are formed in a substantially circular form as seen from the Z1 direction.

<Silicone Seal>

Figure 15:
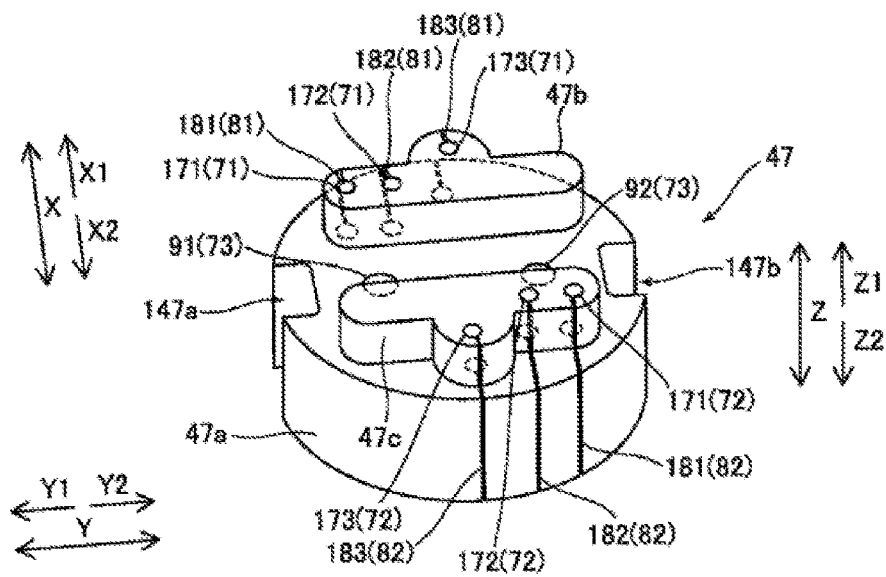
FIG. 15 is a diagram illustrating a perspective view of a silicone seal of the surgical instrument according to a first embodiment.

As illustrated in FIGS. 14 and 15, the silicone seal 47 is inserted in the inner space 8 of the second support body 46. The silicone seal 47 is arranged in an end section on the Z1 side of the inner space 8 of the second support body 46. The silicone seal 47 is closely attached to a section close to the inner space 8 of the end surface 7 of the second support body 46. The silicone seal 47 is configured to seal (close) the first communication hole 61 and the second communication hole 62. Specifically, the silicone seal 47 includes a first seal section 47a, a second seal section 47b, and a third seal section 47c. The silicone seal 47 is an example of a seal member.

The first seal section 47a is formed in an H-shape as seen from the Z1 direction. The first seal section 47a is closely attached to a section on the Z1 side of the inner space 8 of the second support body 46. A first insertion groove 147a and a second insertion groove 147b are formed on the first seal section 47a, and projections on an inner surface of the side surface 6 of the second support body 46 facing the inner space 8 are respectively inserted into the first insertion groove 147a and the second insertion groove 147b. On the first seal section 47a, the second seal section 47b is arranged on the X1 side, and the third seal section 47c is arranged on the X2 side.

The second seal section 47b is formed correspondingly to the first communication hole 61 of the second support body 46. Specifically, the second seal section 47b is formed in a substantial T-shape as seen from the Z1 direction correspondingly to the shape of the first communication hole 61 as seen from the Z1 direction. The second seal section 47b protrudes in the Z1 direction from the first seal section 47a correspondingly to the depth in the Z direction of the first communication hole 61.

The third seal section 47c is formed correspondingly to the second communication hole 62 of the second support body 46. Specifically, the third seal section 47c is formed in a substantial T-shape as seen from the Z1 direction correspondingly to the shape of the second communication hole 62 as seen from the Z1 direction. The third seal section 47c protrudes in the Z1 direction from the first seal section 47a correspondingly to the depth in the Z direction of the second communication hole 62.

The silicone seal 47 includes a first insertion hole group 71, a second insertion hole group 72, and a third insertion hole group 73. The first insertion hole group 71 is provided to pass through the first seal section 47a and the second seal section 47b in the Z direction. The second insertion hole group 72 is provided to pass through the first seal section 47a and the third seal section 47c in the Z direction. The third insertion hole group 73 is provided to pass through only the first seal section 47a in the Z direction.

The first insertion hole group 71 and the second insertion hole group 72 each include a first insertion hole 171 through which the wire W of the first elongated element 1 is inserted, a second insertion hole 172 through which the wire W of the second elongated element 2 is inserted, and a third insertion hole 173 through which the wire W of the third elongated element 3 is inserted. Consequently, the third elongated element 3 can be easily moved while the silicone seal 47 prevents the entrance of foreign material inside the second support body 46.

Inner surfaces of the first insertion hole 171, the second insertion hole 172, and the third insertion hole 173 are closely attached to the wires W of the first elongated element 1, the second elongated element 2, and the third elongated element 3, respectively. The third insertion hole group 73 includes a fourth insertion hole 91 and a fifth insertion hole 92 through which electric wires are inserted to supply power to the end effector 41. The inner surfaces of the fourth insertion hole 91 and the fifth insertion hole 92 are closely attached to the electric wires, respectively. The third insertion hole 173 is an example of an insertion hole.

The silicone seal 47 includes a first slit group 81 and a second slit group 82.

The first slit group 81 includes a first slit 181 that is connected to the first insertion hole 171 of the first insertion hole group 71 and guides the wire W of the first elongated element 1 to the first insertion hole 171 of the first insertion hole group 71. The first slit group 81 includes a second slit 182 that is connected to the second insertion hole 172 of the first insertion hole group 71 and guides the wire W of the second elongated element 2 to the second insertion hole 172 of the first insertion hole group 71. The first slit group 81 includes a third slit 183 that is connected to the third insertion hole 173 of the first insertion hole group 71 and guides the wire W of the third elongated element 3 to the third insertion hole 173 of the first insertion hole group 71. The third slit 183 of the first insertion hole group 71 is an example of a slit.

Likewise, the second slit group 82 includes a first slit 181 that is connected to the first insertion hole 171 of the second insertion hole group 72 and guides the wire W of the first elongated element 1 to the first insertion hole 171 of the second insertion hole group 72. The second slit group 82 includes a second slit 182 that is connected to the second insertion hole 172 of the second insertion hole group 72 and guides the wire W of the second elongated element 2 to the second insertion hole 172 of the second insertion hole group 72. The second slit group 82 includes a third slit 183 that is connected to the third insertion hole 173 of the second insertion hole group 72 and guides the wire W of the third elongated element 3 to the third insertion hole 173 of the second insertion hole group 72. The third slit 183 of the second insertion hole group 72 is an example of a slit.

Since the wire W is inserted into the third insertion hole 173 through the third slit 183, it is unnecessary to attach the third elongated element 3 to the silicone seal 47 in advance. Consequently, the efficiency of assembly works of the surgical instrument 40 can be further improved.

The first slit 181 of the first slit group 81 extends in the X1 direction from the first insertion hole 171. The second slit 182 of the first slit group 81 extends in the X1 direction from the second insertion hole 172. The third slit 183 of the first slit group 81 extends in the X1 direction from the third insertion hole 173. The first slit 181 of the second slit group 82 extends in the X2 direction from the first insertion hole 171. The second slit 182 of the second slit group 82 extends in the X2 direction from the second insertion hole 172. The third slit 183 of the second slit group 82 extends in the X2 direction from the third insertion hole 173.

<Shaft>

Figure 16:
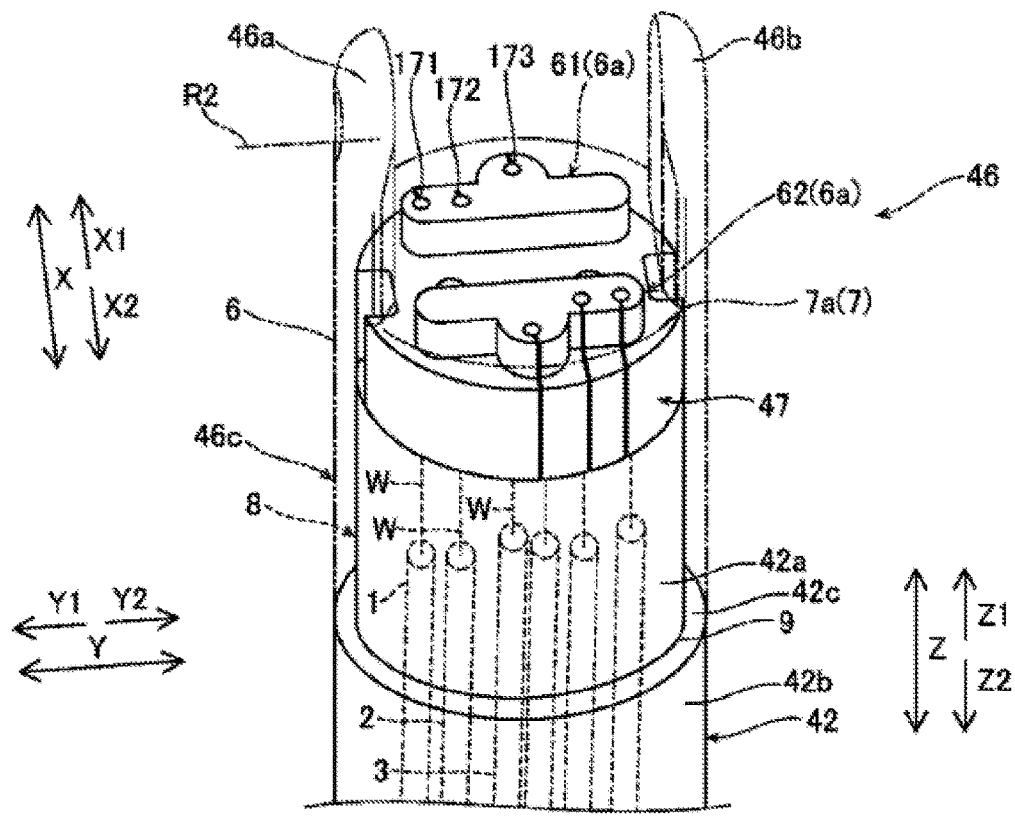
FIG. 16 is a diagram illustrating a perspective view of a state where a connection section of a shaft is inserted in the second support body of the surgical instrument according to a first embodiment.

As illustrated in FIG. 16, the shaft 42 is formed in a cylindrical shape extending along the Z direction. The first elongated element 1, the second elongated element 2, and the third elongated element 3 are housed in the space inside the shaft 42. The shaft 42 includes the cylindrical connection section 42a and a cylindrical body section 42b. The connection section 42a protrudes in the Z1 direction from an end section on the Z1 side of the body section 42b. The body section 42b extends in the Z direction. The shaft 42 includes a step 42c between the connection section 42a and the body section 42b. The step 42c of the shaft 42 comes into contact with an end section on the Z2 side of the side surface 6 of the second support body 46.

As described above, the connection section 42a is connected to the second support body 46. Specifically, the connection section 42a is inserted in the inner space 8 of the second support body 46. In this state, the silicone seal 47 is compressed between the partition 7a and the connection section 42a. This allows the silicone seal 47 to more tightly seal the first communication hole 61 and the second communication hole 62. Additionally, the silicone seal 47 can be more rigidly closely attached to the wire W of the first elongated element 1 passing through the first insertion hole 171, the wire W of the second elongated element 2 passing through the second insertion hole 172, and the wire W of the third elongated element 3 passing through the third insertion hole 173. Consequently, the sealing capability of the silicone seal 47 can be improved.

(Method of Assembling Surgical Instrument)

Hereinafter, a method of assembling the above-described surgical instrument 40 is described with reference to FIGS. 17 to 23.

Figure 17:
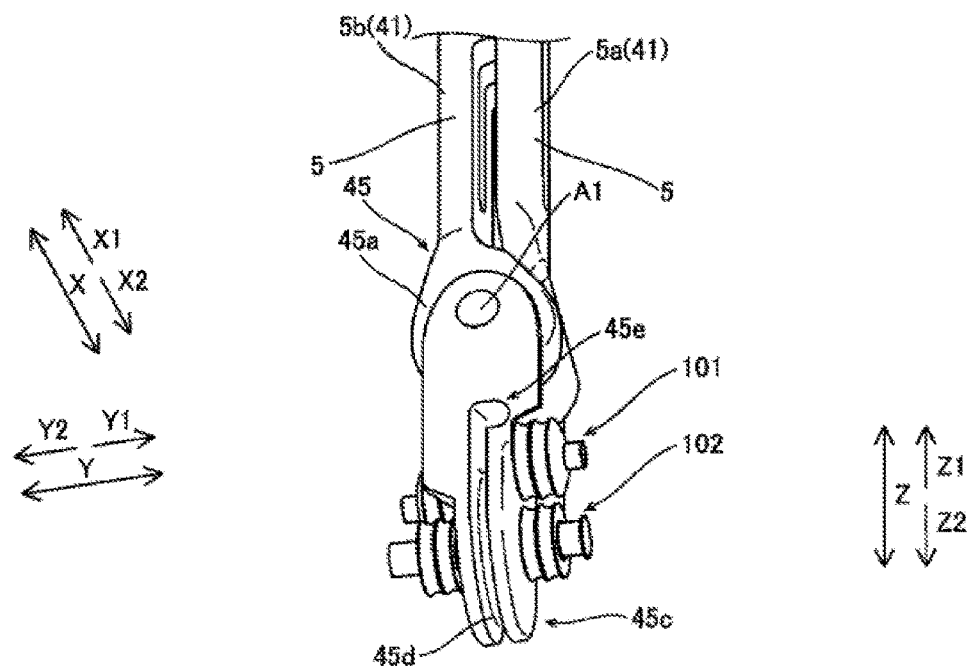
FIG. 17 is a diagram illustrating a perspective view of a state where an end effector and the first support body of the surgical instrument are assembled together according to a first embodiment.
Figure 18:
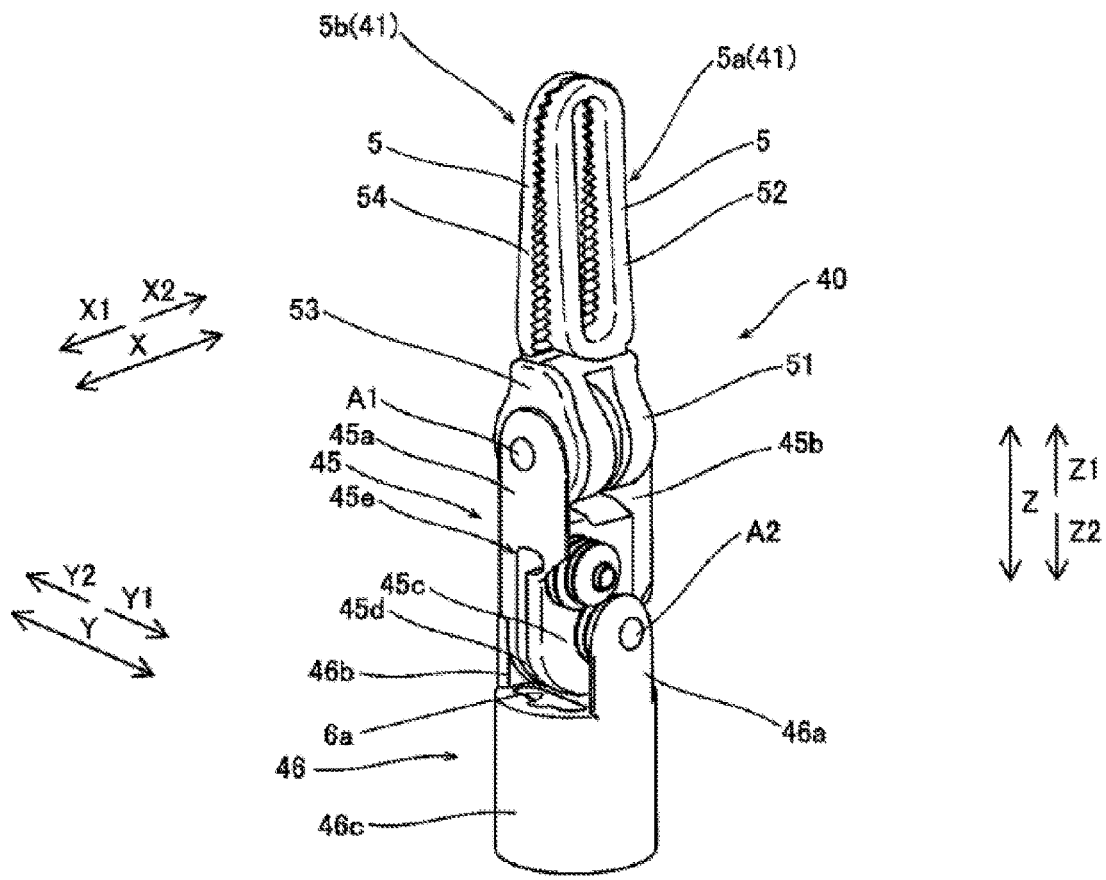
FIG. 18 is a diagram illustrating a perspective view of a state where the end effector, the first support body, and the second support body of the surgical instrument are assembled together according to a first embodiment.

As illustrated in FIG. 17, the end effector 41 is supported by the first support body 45 rotatably about the first shaft A1. The first pulley group 101 and the second pulley group 102 are rotatably attached to the first support body 45. As illustrated in FIG. 18, the first support body 45 is supported by the second support body 46 rotatably about the second shaft A2.

Figure 19:
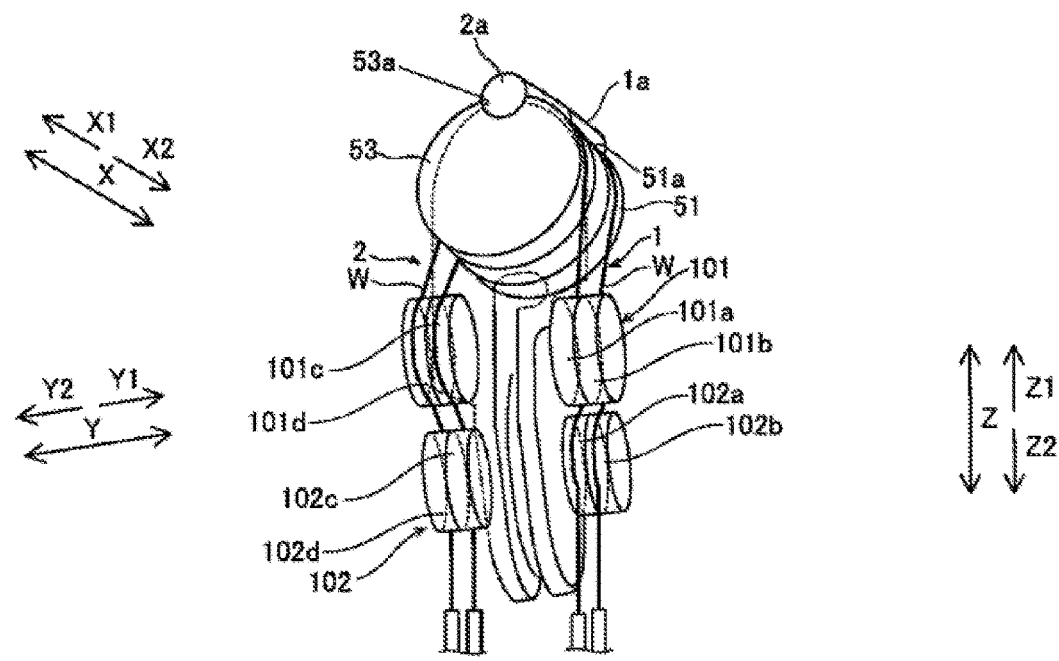
FIG. 19 is a diagram illustrating a schematic view of a state where a first elongated element and a second elongated element are suspended across the first pulley section, the second pulley section, a first pulley group, and a second pulley group of the surgical instrument according to a first embodiment.

As illustrated in FIG. 19, the wire W of the first elongated element 1 is suspended across an X2 side part of the second inner pulley section 102c, which is on the Y2 side of the second pulley group 102, and an X1 side part of the first inner pulley section 101c, which is on the Y2 side of the first pulley group 101. The attachment 1a of the first elongated element 1 is fixed to the wire W of the first elongated element 1 and is fitted to the first recess 51a of the first pulley section 51. The wire W of the first elongated element 1 is suspended across an X2 side part of the first outer pulley section 101b, which is on the Y1 side of the first pulley group 101, and an X1 side part of the second outer pulley section 102b, which is on the Y1 side of the second pulley group 102. Likewise, the wire W of the second elongated element 2 is suspended across the second outer pulley section 102d of the second pulley group 102, the first outer pulley section 101d of the first pulley group 101, the second pulley section 53, the first inner pulley section 101a of the first pulley group 101, and the second inner pulley section 102a of the second pulley group 102 in this order.

Figure 20:
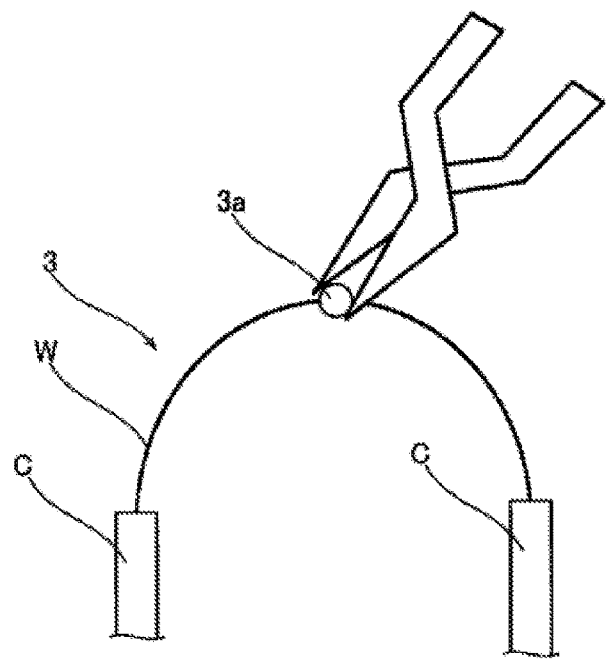
FIG. 20 is a diagram illustrating a schematic view of a state where a third elongated element of the surgical instrument is assembled; according to a first embodiment
Figure 21:
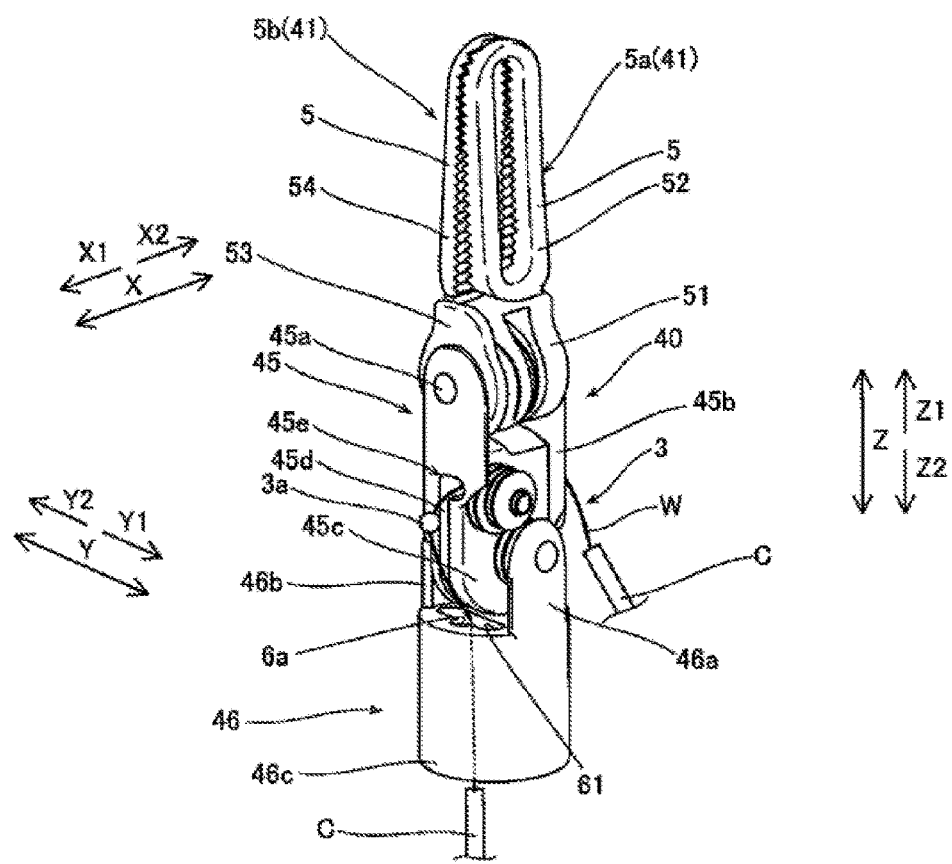
FIG. 21 is a diagram illustrating a perspective view of a state where the third elongated element is inserted through a through-hole in the surgical instrument according to a first embodiment.
Figure 22:
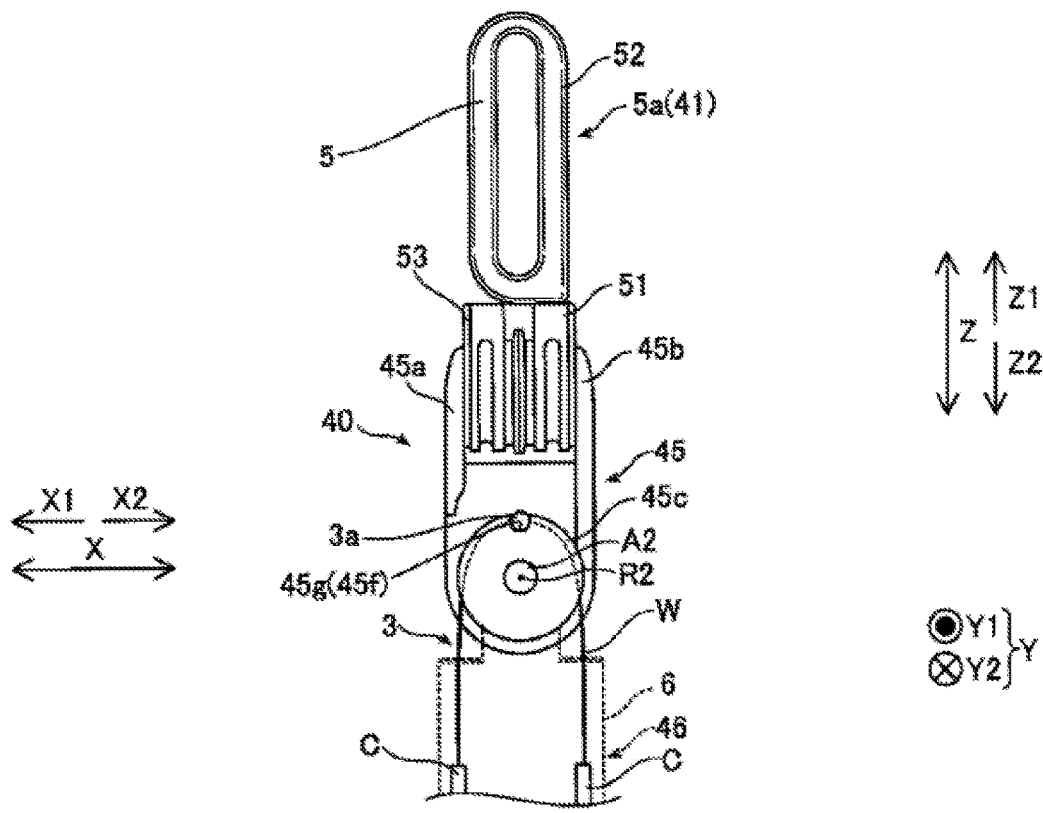
FIG. 22 is a diagram illustrating a schematic view of a state where the third elongated element is engaged with a third pulley section of the surgical instrument according to a first embodiment.

As illustrated in FIG. 20, the third elongated element 3 in which the protection tubes C are fixed to the wire W and the attachment 3a is fixed (crimped) to the wire W is prepared. As illustrated in FIGS. 21 and 22, the third elongated element 3 in which the attachment 3a of the third elongated element 3 and the protection tubes C are fixed to the wire W is attached to the first support body 45 by inserting the third elongated element 3 through the through-hole 45e of the first support body 45 having the size large enough to insert the attachment 3a of the third elongated element 3 and the protection tubes C. Specifically, the attachment 3a of the third elongated element 3 and one protection tube C are inserted through the first communication hole 61, and the one protection tube C is also inserted through the through-hole 45e. Then, the attachment 3a of the third elongated element 3 is inserted through the through-hole 45e, and the one protection tube C is inserted through the second communication hole 62 (see FIG. 14). In this state, the wire W of the third elongated element 3 is drawn in the Z2 direction, and the attachment 3a of the third elongated element 3 is engaged with the engagement section 45f of the third pulley section 45c.

Figure 23:
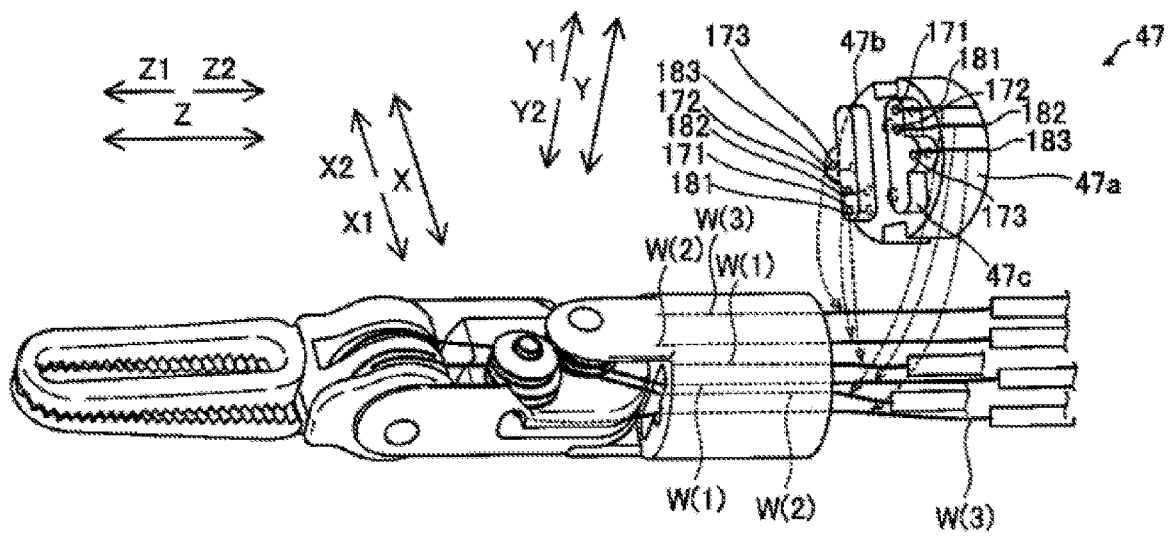
FIG. 23 is a diagram illustrating a schematic view of a state where the first to third elongated elements are attached to the silicone seal of the surgical instrument according to a first embodiment.

As illustrated in FIG. 23, the wire W of the first elongated element 1 is inserted through the first slit 181 of the first slit group 81 and is inserted into the first insertion hole 171 of the first insertion hole group 71. The wire W of the first elongated element 1 is also inserted through the first slit 181 of the second slit group 82 and is inserted into the first insertion hole 171 of the second insertion hole group 72. The same processes are performed on the second elongated element 2 and the third elongated element 3. The wire W of the second elongated element 2 is inserted into the second insertion hole 172 of the first insertion hole group 71 and the second insertion hole 172 of the second insertion hole group 72. The wire W of the third elongated element 3 is inserted into the third insertion hole 173 of the first insertion hole group 71 and the third insertion hole 173 of the second insertion hole group 72.

The second seal section 47b and the third seal section 47c of the silicone seal 47 are respectively inserted into the first communication hole 61 and the second communication hole 62. Consequently, the silicone seal 47 seals the inner space 8 of the second support body 46. In this way, the surgical instrument 40 is assembled.

Second Embodiment

Next, with reference to FIGS. 24 to 35, a second embodiment is described. A second embodiment is different from an above-described first embodiment in which the number of the end effector member 5 of the end effector 41 is two, and an example of a configuration in which the number of an end effector member 205 of an end effector 241 is one is described in a second embodiment. In the drawings, the similar configurations as those of an above-described first embodiment are indicated by the same reference signs.

(Surgical Instrument)

Figure 24:
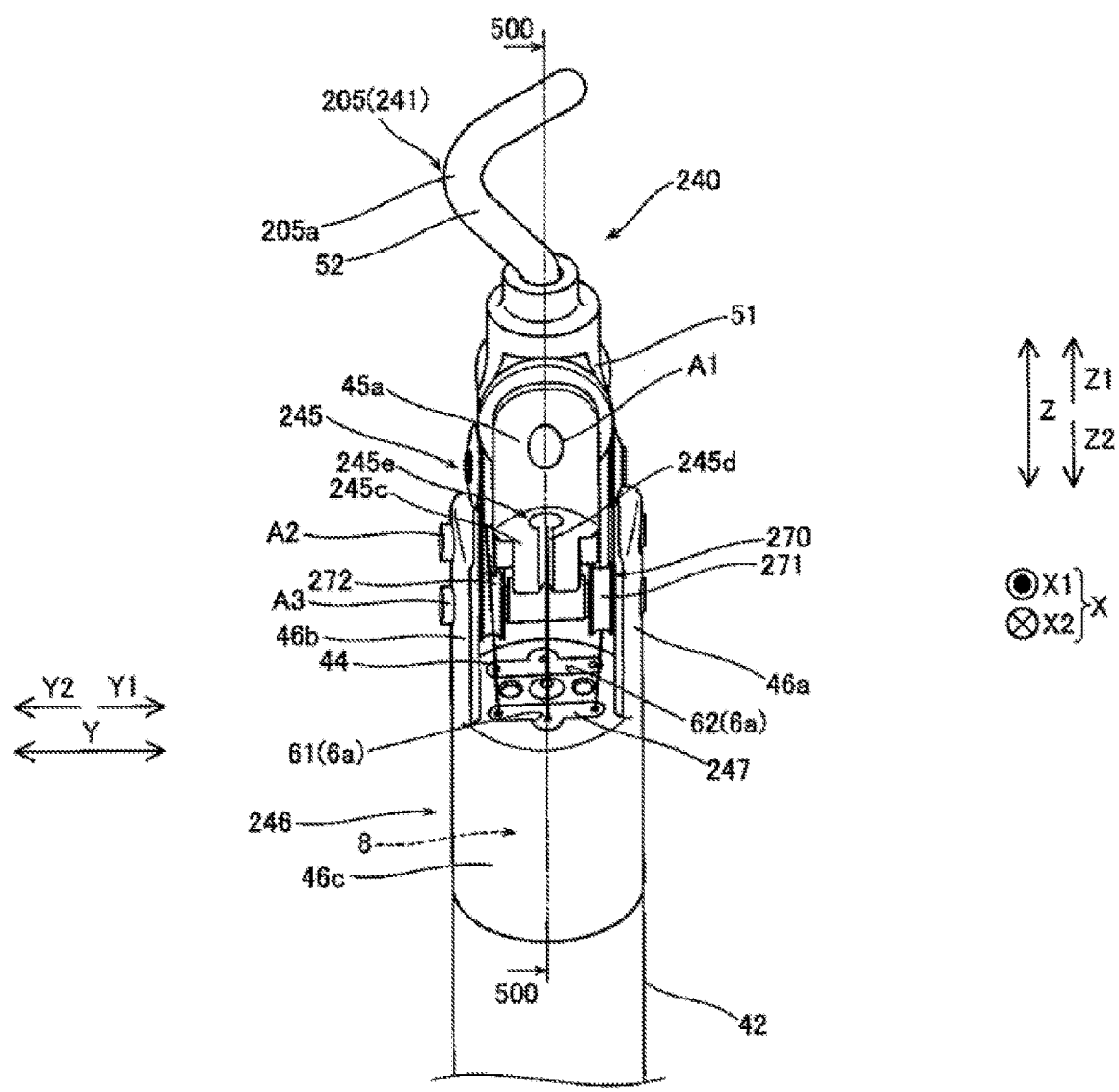
FIG. 24 is a diagram illustrating a perspective view of a surgical instrument according to a second embodiment.

As illustrated in FIG. 24, a surgical instrument 240 is configured to operate the end effector 241 at a tip section or a distal end portion of the surgical instrument 240 by driving of elongated elements 44 that are driven by a (not-illustrated) drive mechanism in a robot arm 21. Specifically, the surgical instrument 240 includes the elongated elements 44, the above-described end effector 241, a first support body 245, a second support body 246, a silicone seal 247, and a shaft 42.

The end effector 241 is configured to perform procedures of the surgery site of the patient P based on the function of a type of the end effector 241. Specifically, the end effector 241 includes a single end effector member 205. The end effector member 205 is a hook 205a. The hook 205a is attached to the first support body 245.

Figure 25A:
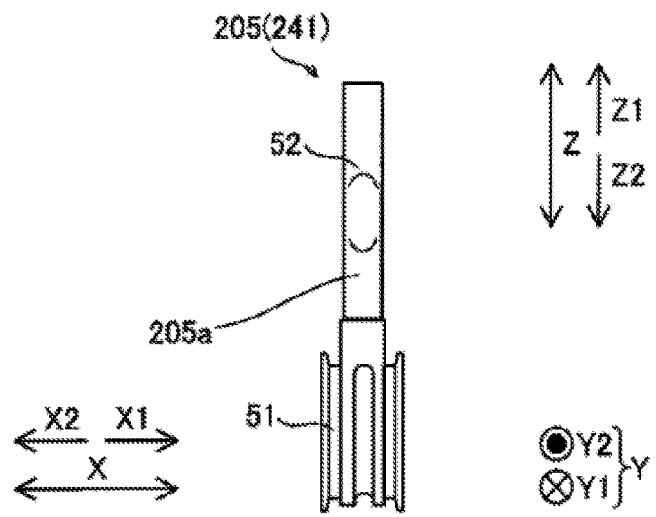
FIG. 25A is a diagram illustrating a schematic view of a hook.
Figure 25B:
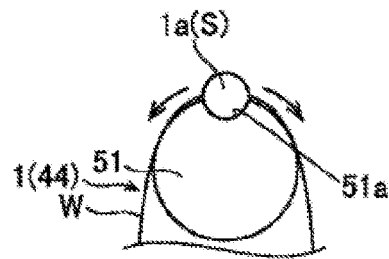
FIG. 25B is a diagram illustrating a schematic view of a first pulley section.

As illustrated in FIGS. 25A and 25B, the hook 205a includes a first pulley section 51 and a first procedure section 52. The first pulley section 51 forms a first recess 51a engaged with an attachment S of one of the elongated elements 44 (hereinafter, an attachment 1a of a first elongated element 1). The first procedure section 52 changes the orientation by rotation of the first pulley section 51 in accordance with movement of the first elongated element 1.

(First Support Body)

Figure 26:
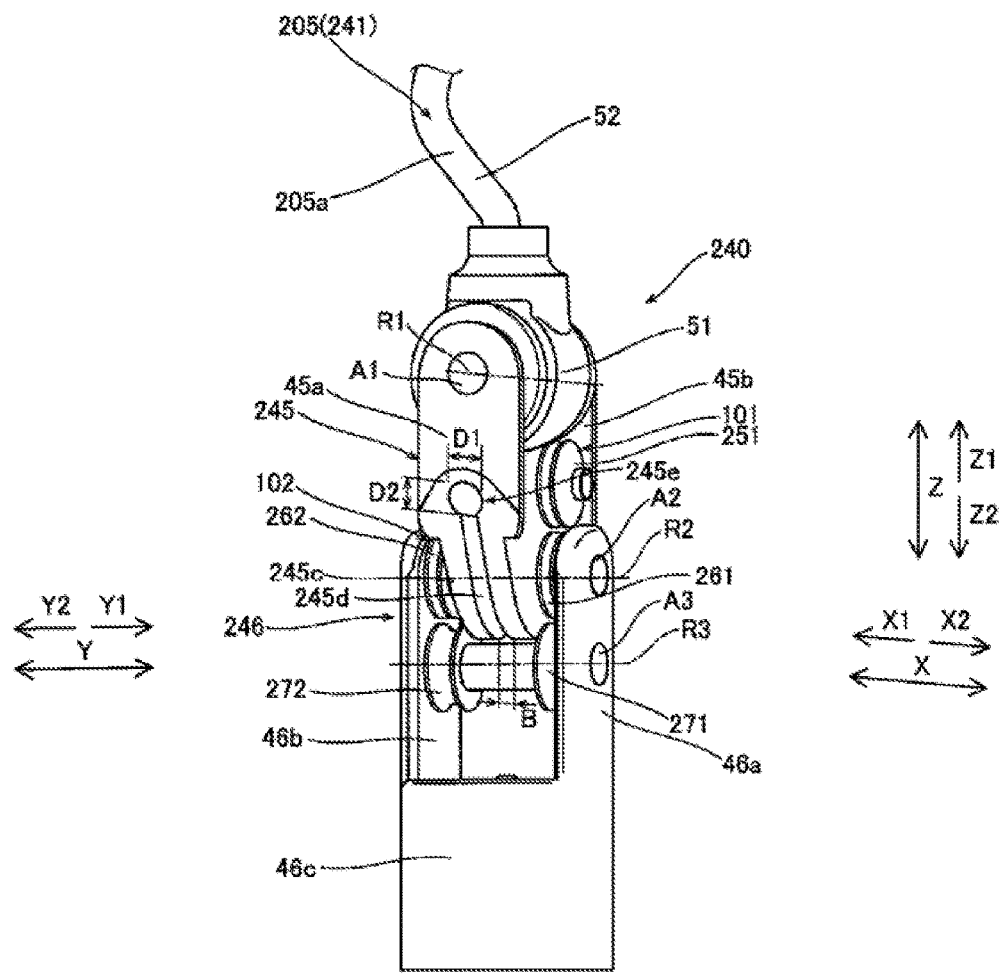
FIG. 26 is a diagram illustrating a perspective view of the surgical instrument according to a second embodiment as seen from the X1 direction.

As illustrated in FIG. 26, the first support body 245 includes a first protrusion section 45a, a second protrusion section 45b, and a second pulley section 245c. The first protrusion section 45a protrudes in the Z1 direction from an end section on the X1 side of the second pulley section 245c. The first protrusion section 45a supports an end section on the X1 side of a first shaft A1. The second protrusion section 45b protrudes in the Z1 direction from an end section on the X2 side of the second pulley section 245c. The second protrusion section 45b supports an end section on the X2 side of the first shaft A1. The second pulley section 245c is rotatably supported by a second shaft A2. The second pulley section 245c includes a pulley groove 245d formed along a circumferential direction of the second shaft A2. The second pulley section 245c is an example of a pulley section.

<Through-Hole>

The first support body 245 of a second embodiment includes a through-hole 245e having the size large enough to insert the attachment S of one of the elongated elements 44 (hereinafter, an attachment 203a of a second elongated element 203) and protection tubes C. Specifically, the through-hole 245e is formed to allow insertion therethrough of the second elongated element 203 in which the attachment 203a and the protection tubes C are fixed to a wire W.

Specifically, the through-hole 245e has a predetermined width D1 in the Y direction and a predetermined height D2 in the Z direction. The predetermined width D1 of the through-hole 245e is greater than a width B in the Y direction of the pulley groove 245d of the second pulley section 245c. The predetermined width D1 of the through-hole 245e is smaller than the maximum width in the Y direction of the second pulley section 245c. The predetermined height D2 of the through-hole 245e is greater than lengths of the protection tubes C and the attachment 203a of the second elongated element 203 in a direction orthogonal to the direction in which the wire W extends. The predetermined height D2 of the through-hole 245e is smaller than a length in the Z direction of the first shaft A1. The through-hole 245e is formed in a circular shape as seen from the X1 direction. Specifically, the predetermined height D2 and the predetermined width D1 are substantially equal to each other in the through-hole 245e.

Figure 27:
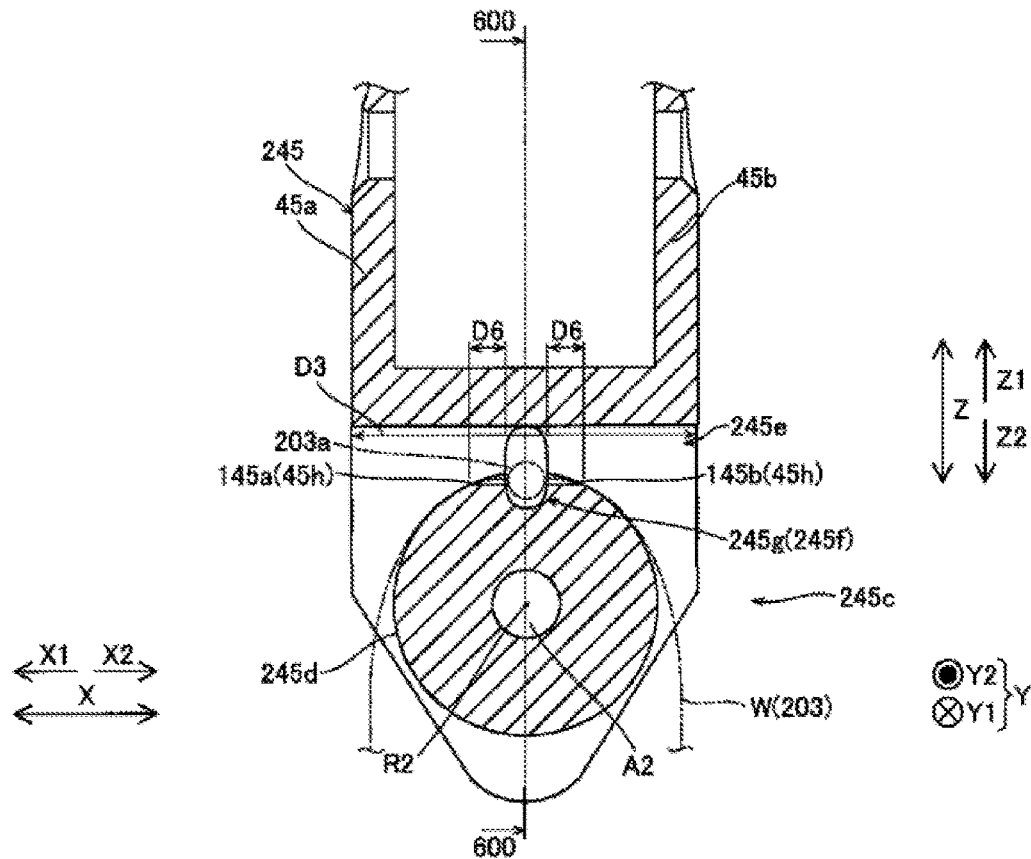
FIG. 27 is a diagram illustrating a cross-sectional view taken along the 500-500 line in FIG. 24.

As illustrated in FIG. 27, the through-hole 245e is configured to linearly pass through the first support body 245 along the X direction. Specifically, the through-hole 245e is formed in an end section on the Z1 side of the second pulley section 245c. The through-hole 245e is connected to a section on the Z1 side of the pulley groove 245d of the second pulley section 245c. The through-hole 245e has a predetermined length D3 in the X direction. The predetermined length D3 of the through-hole 245e is substantially equal to the maximum length in the X direction of the second pulley section 245c.

<Engagement Section>

Figure 28:
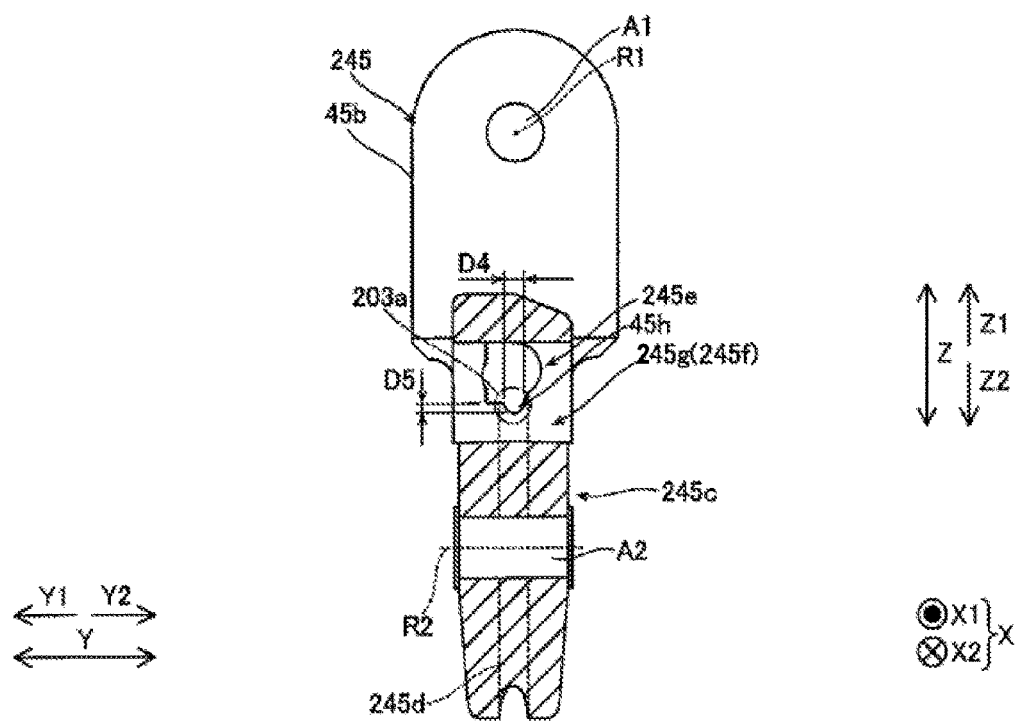
FIG. 28 is a diagram illustrating a cross-sectional view taken along the 600-600 line in FIG. 27.

As illustrated in FIGS. 27 and 28, the first support body 245 includes an engagement section 245f that is provided in the second pulley section 245c and engaged with the attachment 203a of the second elongated element 203 inserted through the through-hole 245e. The engagement section 245f is configured to be engaged with the attachment 203a of the second elongated element 203 to allow rotation of the second pulley section 245c about the rotation axis R2 of the second shaft A2 with the movement of the second elongated element 203.

Specifically, the engagement section 245f includes a second recess 245g to which the attachment 203a of the second elongated element 203 is fitted. The attachment 203a of the second elongated element 203 is formed in a spherical shape. The second recess 245g of the engagement section 245f is formed in a shape along the attachment 203a of the second elongated element 203. Specifically, the second recess 245g of the engaged section 245f is formed in a substantially semicircular shape as seen from the Y direction. For example, the second recess 245g may be formed in a semispherical or semi-column shape.

The through-hole 245e is formed so as to linearly extend along the X direction and be connected to the second recess 245g of the engagement section 245f. Specifically, the second recess 245g is a recess in the Z2 direction on a bottom surface of the section on the Z1 side of the pulley groove 245d of the second pulley section 245c.

<Wire Groove Section>

As illustrated in FIG. 28, the second pulley section 245c includes a wire groove section 45h, which is a recess in the Z2 direction on a bottom surface of an end section on the Z1 side of the pulley groove 245d of the second pulley section 245c. The wire groove section 45h is configured such that the wire W is fitted thereto when the attachment S is engaged with the engagement section 245f.

Specifically, the wire groove section 45h has a predetermined width D4 in the Y direction and a predetermined depth D5 in the Z direction. The predetermined width D4 of the wire groove section 45h is smaller than a width B (see FIG. 26) in the Y direction of the pulley groove 245d of the second pulley section 245c. The predetermined depth D5 of the wire groove section 45h is greater than the diameter of the wire W. The center position in the Y direction of the wire groove section 45h is located so as to substantially coincide with the center position in the Y direction of the pulley groove 245d of the second pulley section 245c.

An end section on the Z1 side of the wire groove section 45h is provided to continue to the through-hole 245e. Specifically, the wire groove section 45h is connected to the through-hole 245e in the Z direction.

As illustrated in FIG. 27, the wire groove section 45h is configured to guide the wire W in the circumferential direction of the pulley groove 245d of the second pulley section 245c when the attachment 203a of the second elongated element 203 is engaged with the engagement section 245f. Specifically, the wire groove section 45h has a predetermined length D6 in the X direction. The wire groove section 45h is provided in sections adjacent to the second recess 245g in the circumferential direction and extends along the Y direction. Specifically, the wire groove section 45h includes a first groove section 145a provided in the X1 side and a second groove section 145b provided in the X2 side.

As illustrated in FIG. 26, the first support body 245 includes a first pulley group 101 and a second pulley group 102 that guide the first elongated element 1 engaged with the first pulley section 51. The first pulley group 101 is arranged in the Z1 side of the second shaft A2. The second pulley group 102 is arranged in the second shaft A2.

Figure 32:
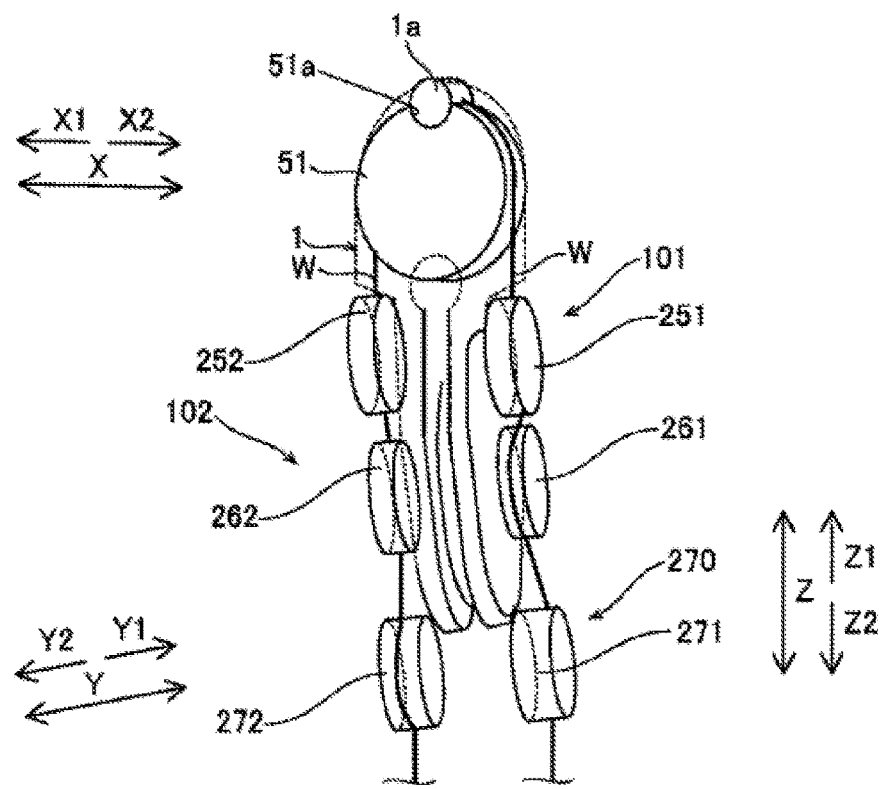
FIG. 32 is a diagram illustrating a schematic view of a state where a first elongated element is suspended across a first pulley section, a first pulley group, a second pulley group, and a third pulley group of the surgical instrument according to a second embodiment.

The first pulley group 101 includes a first guide pulley section 251 in the Y1 side and a second guide pulley section 252 in the Y2 side (see FIG. 32). The second pulley group 102 includes a third guide pulley section 261 in the Y1 side and a fourth guide pulley section 262 adjacent to the second pulley section 245c.

(Second Support Body)

As illustrated in FIG. 24, the second support body 246 includes a third protrusion section 46a, a fourth protrusion section 46b, and a connection base section 46c. The third protrusion section 46a protrudes in the Z1 direction from an end section on the Y1 side of the connection base section 46c. The third protrusion section 46a supports an end section on the Y1 side of the second shaft A2. The third protrusion section 46a supports an end section on the Y1 side of a third shaft A3 arranged in the Z2 side of the second shaft A2. The fourth protrusion section 46b protrudes in the Z1 direction from an end section on the Y2 side of the connection base section 46c. The fourth protrusion section 46b supports an end section on the Y2 side of the second shaft A2. The fourth protrusion section 46b supports an end section on the Y2 side of the third shaft A3. The third shaft A3 includes an axis that extends in the Y direction like the second shaft A2.

Communication holes 6a are formed to pass through a partition 7a of the connection base section 46c in the extending direction of the shaft 42 (the Z direction). The communication holes 6a allow communication between an inner space 8 of the connection base section 46c and the outer space of the connection base section 46c. In the partition 7a of the connection base section 46c, a communication hole 6a located in the X1 side (hereinafter, a first communication hole 61) and a communication hole 6a located in the X2 side (hereinafter, a second communication hole 62) are formed.

The second support body 246 includes a third pulley group 270 that guides the first elongated element 1 engaged with the first pulley section 51. The third pulley group 270 is arranged on the third shaft A3. The third pulley group 270 includes a fifth guide pulley section 271 in the Y1 side and a sixth guide pulley section 272 in the Y2 side.

<Silicone Seal>

Figure 29:
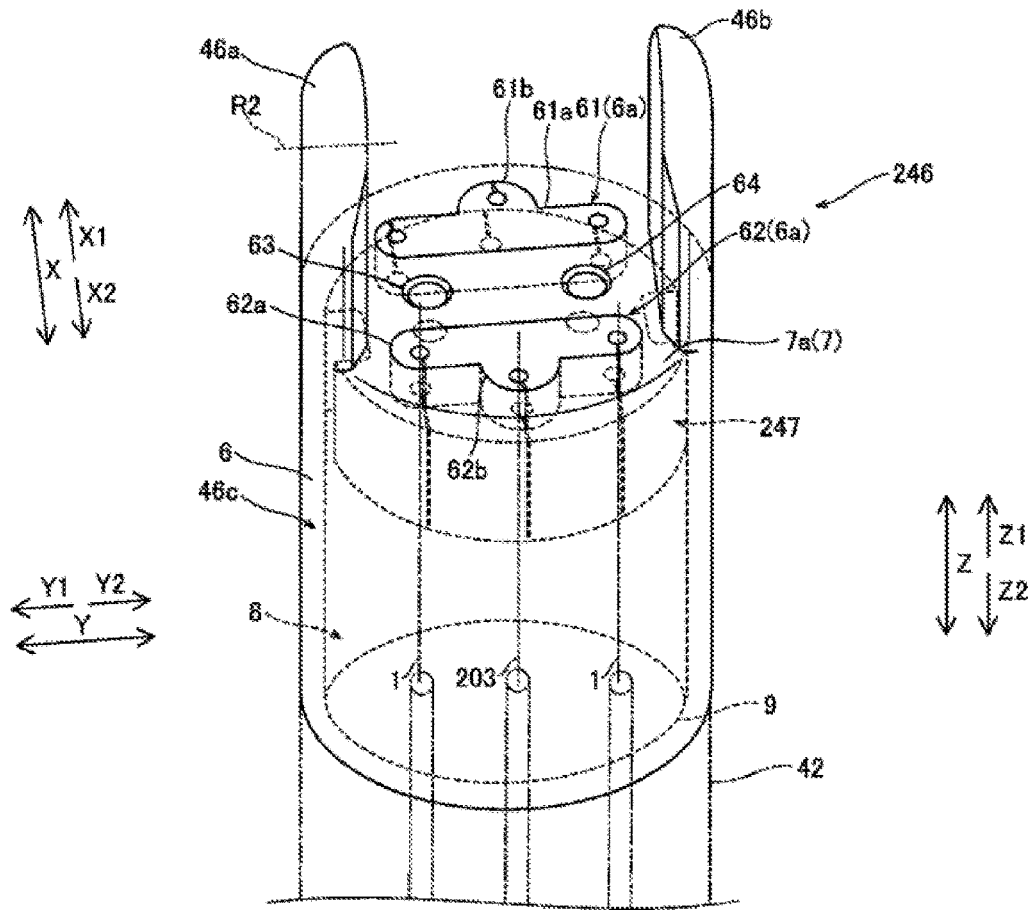
FIG. 29 is a diagram illustrating a perspective view of a second support body of the surgical instrument according to a second embodiment.
Figure 30:
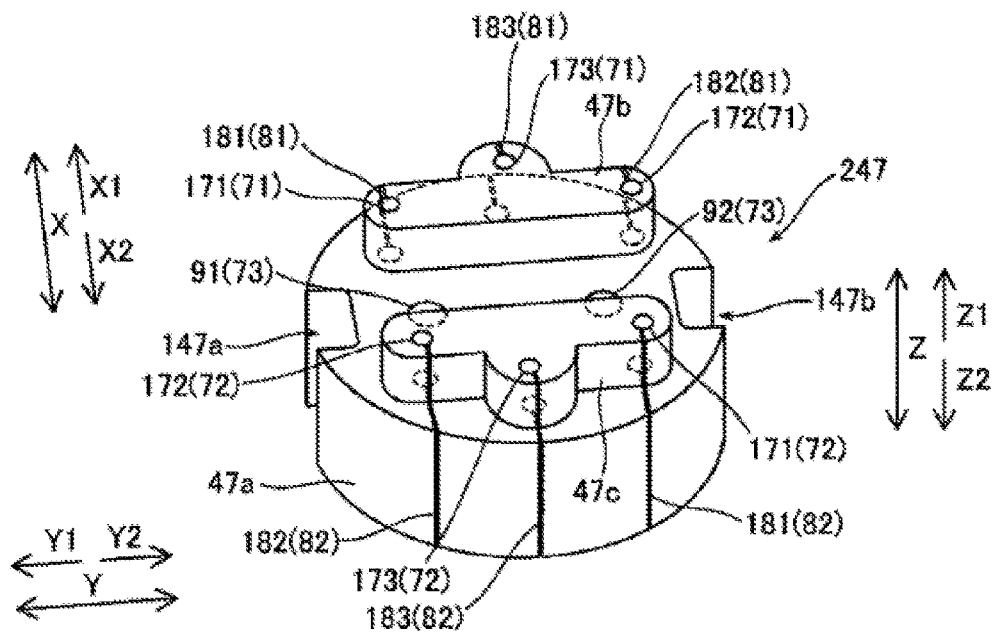
FIG. 30 is a diagram illustrating a perspective view of a silicone seal of the surgical instrument according to a second embodiment.

As illustrated in FIGS. 29 and 30, the silicone seal 247 is inserted in the inner space 8 of the second support body 246. The silicone seal 247 is arranged in an end section on the Z1 side of the inner space 8 of the second support body 246. Specifically, the silicone seal 247 includes a first seal section 47a, a second seal section 47b, and a third seal section 47c. The silicone seal 247 is an example of a seal member.

The silicone seal 247 includes a first insertion hole group 71, a second insertion hole group 72, and a third insertion hole group 73. The first insertion hole group 71 and the second insertion hole group 72 each include a first insertion hole 171 and a second insertion hole 172 through which the wire W of the first elongated element 1 is inserted and a third insertion hole 173 through which the wire W of the second elongated element 203 is inserted. The third insertion hole group 73 includes a fourth insertion hole 91 and a fifth insertion hole 92 through which electric wires are inserted. The third insertion hole 173 is an example of an insertion hole.

The first insertion hole 171 of the first insertion hole group 71 is located in an end section on the Y1 side of the second seal section 47b. The second insertion hole 172 of the first insertion hole group 71 is located in an end section on the Y2 side of the second seal section 47b. The first insertion hole 171 of the second insertion hole group 72 is located in an end section on the Y2 side of the third seal section 47c. The second insertion hole 172 of the second insertion hole group 72 is located in an end section on the Y1 side of the third seal section 47c.

The silicone seal 247 includes a first slit group 81 and a second slit group 82. The first slit group 81 is connected to the first insertion hole 171, the second insertion hole 172, and the third insertion hole 173 of the first insertion hole group 71. The second slit group 82 is connected to the first insertion hole 171, the second insertion hole 172, and the third insertion hole 173 of the second insertion hole group 72. Other configurations of a second embodiment are the same as those of an above-described first embodiment.

(Method of Assembling Surgical Instrument)

Hereinafter, a method of assembling the above-described surgical instrument 240 is described with reference to FIGS. 31 to 35.

Figure 31:
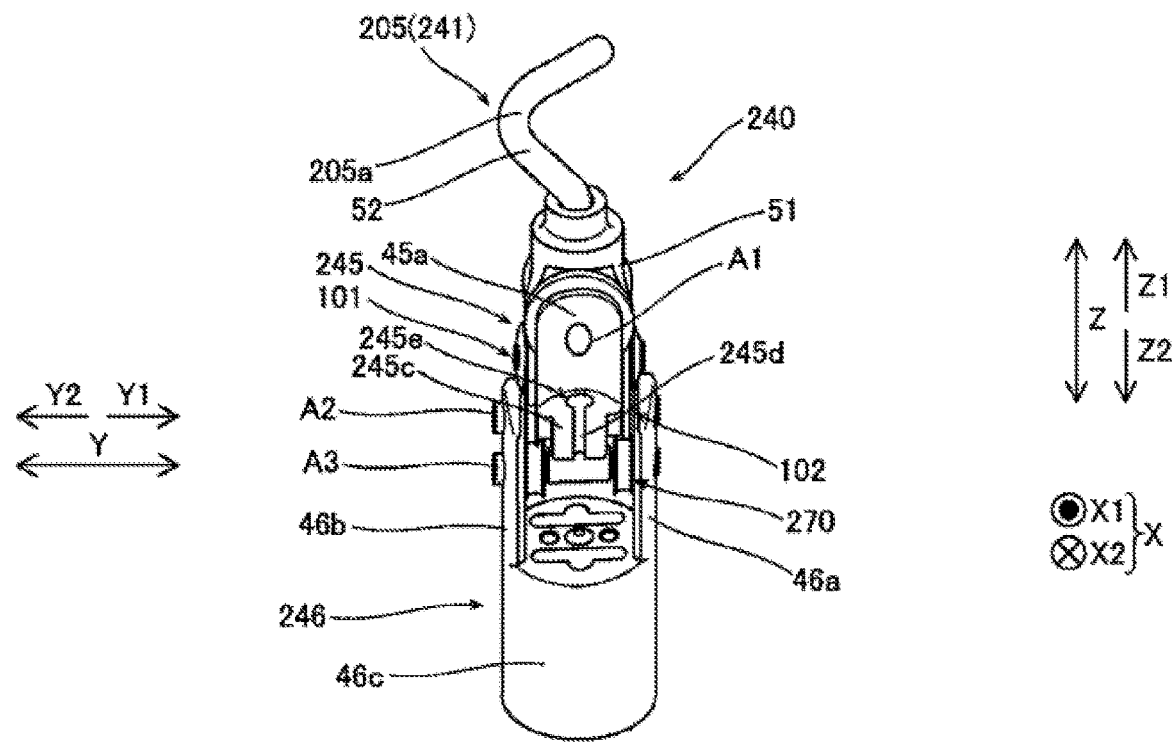
FIG. 31 is a diagram illustrating a perspective view of a state where an end effector, a first support body, and the second support body of the surgical instrument are assembled together according to a second embodiment.

As illustrated in FIG. 31, the end effector 241 is supported by the first support body 245 rotatably about the first shaft A1. The first pulley group 101 and the second pulley group 102 are rotatably attached to the first support body 245. The first support body 245 is supported by the second support body 246 rotatably about the second shaft A2. The third pulley group 270 is attached to the second support body 246 rotatably about the third shaft A3.

As illustrated in FIG. 32, the wire W of the first elongated element 1 is suspended across an X1 side part of the guide pulley section 272, which is on the Y2 side of the third pulley group 270, and an X2 side part of the fourth guide pulley section 262, which is on the Y2 side of the second pulley group 102. The wire W of the first elongated element 1 is suspended across an X2 side part of the second guide pulley section 252, which is in the Y2 side of the first pulley group 101.

The attachment 1a is fixed to the wire W of the first elongated element 1, and the attachment 1a of the first elongated element 1 is fitted to the first recess 51a of the first pulley section 51. The wire W of the first elongated element 1 is suspended across an X2 side part of the first guide pulley section 251, which is in the Y1 side of the first pulley group 101. The wire W of the first elongated element 1 is suspended across an X1 side part of the third guide pulley section 261, which is on the Y1 side of the second pulley group 102, and an X2 side part of the fifth guide pulley section 271, which is on the Y1 side of the third pulley group 270.

Figure 33:
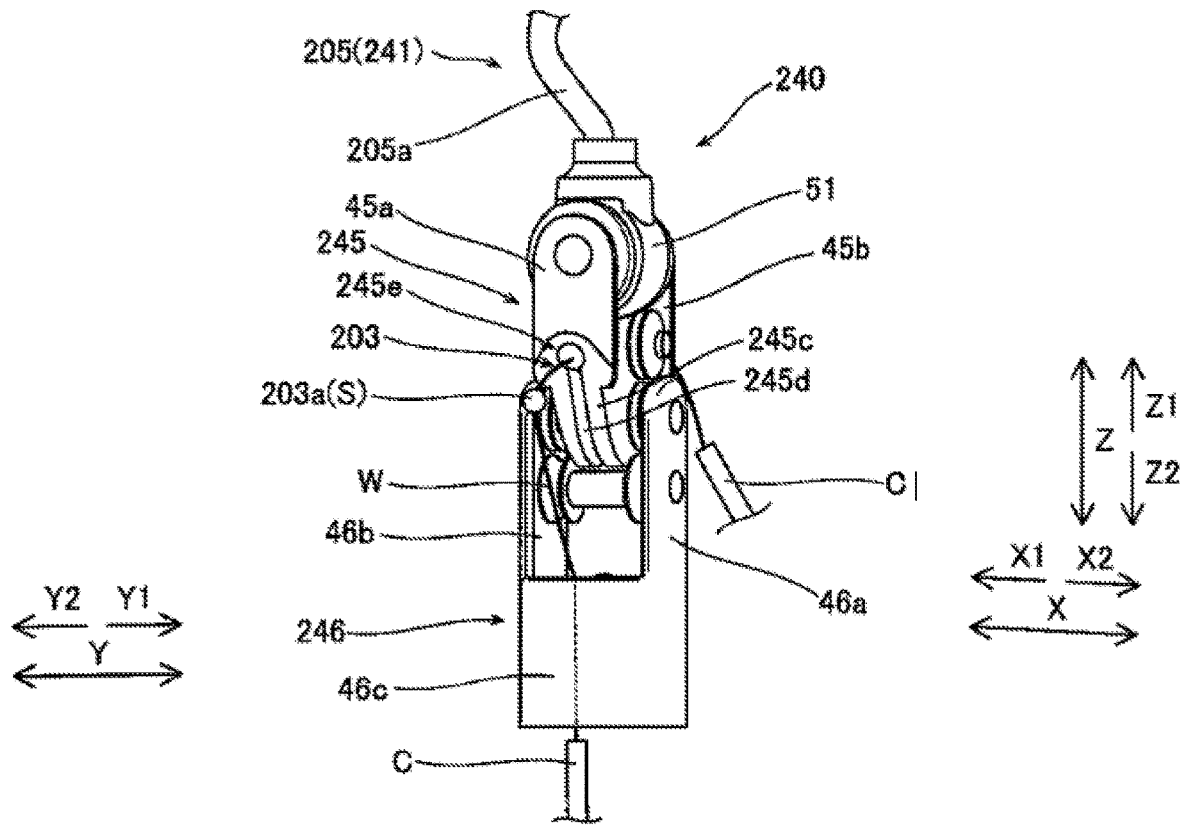
FIG. 33 is a diagram illustrating a perspective view of a state where a second elongated element is inserted through a through-hole in the surgical instrument according to a second embodiment.
Figure 34:
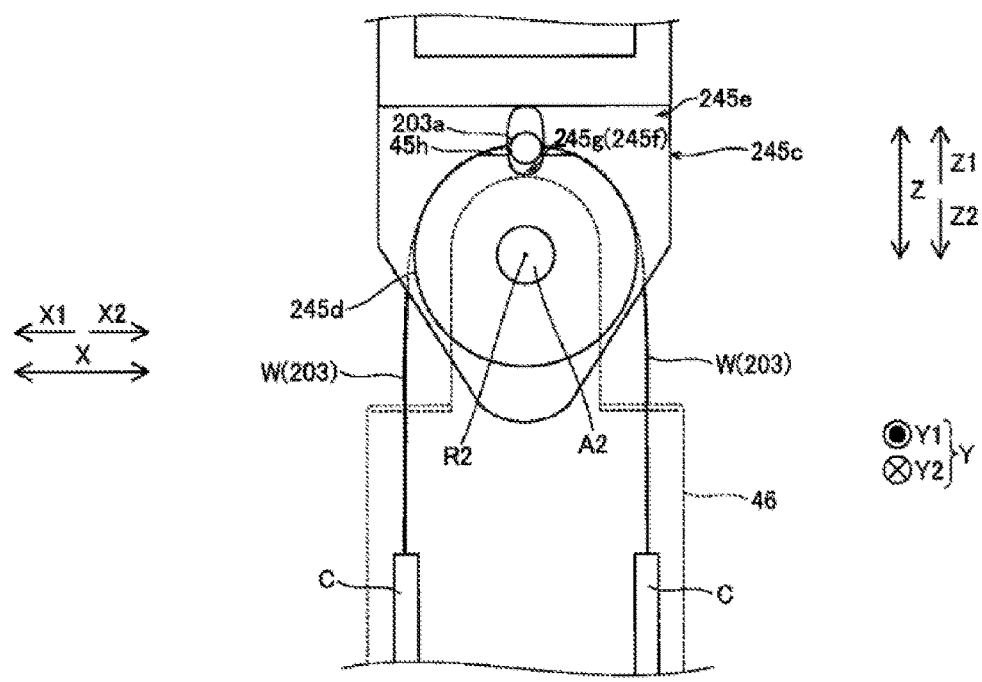
FIG. 34 is a diagram illustrating a schematic view of a state where the second elongated element is engaged with a second pulley section of the surgical instrument according to a second embodiment.

The second elongated element 203 in which the protection tubes C are fixed to the wire W and the attachment 203a is fixed (crimped) to the wire W is prepared. As illustrated in FIGS. 33 and 34, the second elongated element 203 in which the attachment 203a of the second elongated element 203 and the protection tubes C are fixed to the wire W is attached to the first support body 245 by inserting the second elongated element 203 through the through-hole 245e of the first support body 245 having the size large enough to insert the attachment 203a of the second elongated element 203 and the protection tubes C. Specifically, the attachment 203a of the second elongated element 203 and one protection tube C are inserted through the first communication hole 61 (see FIG. 24), and the one protection tube C is also inserted through the through-hole 245e. Then, the attachment 203a of the second elongated element 203 is inserted through the through-hole 245e, and the one protection tube C is inserted through the second communication hole 62 (see FIG. 24). In this state, the wire W of the third elongated element 3 is drawn in the Z2 direction, and the attachment 203a of the second elongated element 203 is engaged with the engagement section 245f of the second pulley section 245c.

Figure 35:
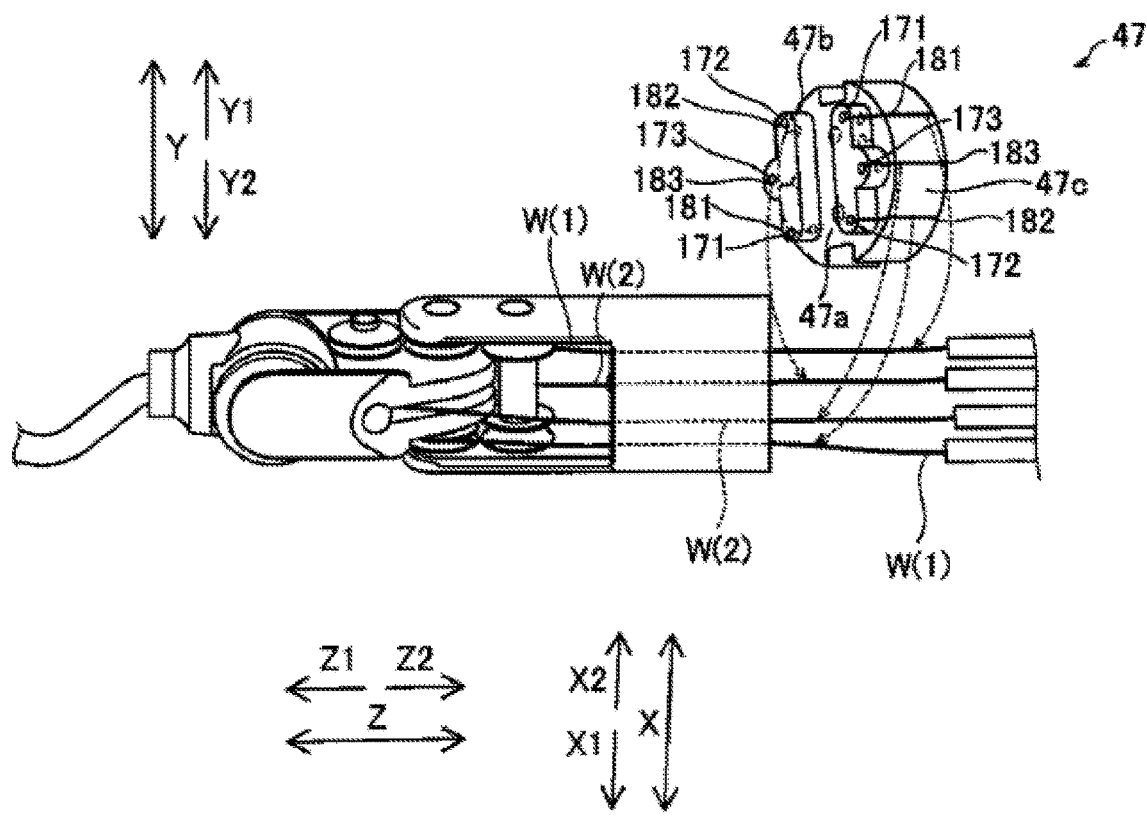
FIG. 35 is a diagram illustrating a schematic view of a state where the first and second elongated elements are attached to the silicone seal of the surgical instrument according to a second embodiment.

As illustrated in FIG. 35, the wire W of the first elongated element 1 is inserted through the first slit 181 of the first slit group 81 and is inserted into the first insertion hole 171 of the first insertion hole group 71. The wire W of the first elongated element 1 is also inserted through the second slit 182 of the first slit group 81 and is inserted into the second insertion hole 172 of the first insertion hole group 71. The same processes are performed on the second elongated element 203. The wire W of the second elongated element 203 is inserted into the third insertion hole 173 of the first insertion hole group 71 and the third insertion hole 173 of the second insertion hole group 72.

The second seal section 47b and the third seal section 47c of the silicone seal 247 are respectively inserted into the first communication hole 61 and the second communication hole 62. Consequently, the silicone seal 247 seals the inner space 8 of the second support body 246. In this way, the surgical instrument 240 is assembled.

As described above, it is possible to improve the efficiency of assembly works of the surgical instrument 240 even in the case where the number of the end effector member is one.

(Modifications)

It should be understood that the above-described embodiments are illustrated by way of example in every respect and do not limit the invention. The scope of the present invention is indicated by claims, not by explanation of the embodiments, and includes equivalents to claims and all alterations (modifications) within the same.

For example, the attachment 3a of the third elongated element and the attachment 203a of the second elongated element 203 are formed in a spherical shape in the examples illustrated in above-described first and second embodiments, but the invention is not limited thereto. The attachment of the third elongated element and the attachment of the second elongated element may be formed in a column shape or the like in an embodiment or a modification.

The second pulley section 245c and the third pulley section 45c each include the wire groove section 45h in the examples illustrated in above-described first and second embodiments, but the invention is not limited thereto. The second pulley section and the third pulley section may not each include the wire groove section in an embodiment or a modification.

The predetermined depth D5 of the wire groove section 45h is greater than the diameter of the wire W in the examples illustrated in above-described first and second embodiments, but the invention is not limited thereto. The predetermined depth of the wire groove section may be equal to or smaller than the diameter of the wire in an embodiment or a modification.

The surgical instrument 40 (240) includes the first jaw 5a and the second jaw 5b or the hook 205a as the end effector member 5 (205) in the examples illustrated in above-described first and second embodiments, but the invention is not limited thereto. The surgical instrument may use grasping forceps, scissors, a high-frequency knife, a snare wire, a clamp, or a stapler as the end effector member in an embodiment or a modification.

The invention claimed is:

1. A robotic surgical instrument, comprising:
an end effector;
a first support body that supports the end effector rotatably about a first shaft;
a second support body that supports the first support body rotatably about a second shaft;
an elongated element to rotate the first support body with respect to the second support body; and
an elongated shaft to which the second support body is connected, wherein
the elongated element includes a wire, two protection tubes fixed to the wire, and an attachment fixed to a middle of the wire between the two protection tubes,
the first support body includes: a pulley section that is rotatably supported by the second shaft and formed with a pulley groove to which the elongated element is configured to be partially wound; a recess that is recessed from the pulley groove in the first support body and to which the attachment is configured to be fitted; and a through-hole extending through the first support body at a position shifted from the recess and having a size through which the attachment and the two protection tubes are passable,
the through-hole is connected to the recess via a communication passage that connects a middle portion of the through-hole in a direction of a length of the through-hole and the recess in the first support body such that when the attachment of the elongated element is inserted in the through-hole, the attachment is movable from the through-hole through the communication passage to the recess and is so as to be engaged with the recess, and
the communication passage comprises a second through-hole extending through the first support body in a direction orthogonal to the length of the through-hole.

2. The robotic surgical instrument according to claim 1, further comprising:
a housing to which the elongated shaft is connected, wherein the housing is configured to be attached to a robot arm.

3. The robotic surgical instrument according to claim 1, wherein
the recess is formed in a shape corresponding to an outer shape of the attachment.

4. The robotic surgical instrument according to claim 1, wherein
the attachment is formed in a spherical shape, and
the recess is formed in a semicircular shape as seen in an axis direction of the second shaft.

5. The robotic surgical instrument according to claim 1, wherein
a width, in an axis direction of the second shaft, of the through-hole is greater than a width, in the axis direction of the second shaft, of the pulley groove of the pulley section.

6. The robotic surgical instrument according to claim 1, wherein
the pulley section includes a wire groove section that is provided in an area adjacent to the recess in a circumferential direction of the pulley section and extends along an axis direction of the first shaft.

7. The robotic surgical instrument according to claim 6, wherein
a depth of the wire groove section is greater than a diameter of the wire.

8. The robotic surgical instrument according to claim 1, wherein
the through-hole linearly extends along an axis direction of the first shaft.

9. The robotic surgical instrument according to claim 1, wherein
the second support body includes a connection base section that is connected to the elongated shaft and a first protrusion section and a second protrusion section that protrude from a first end portion of the connection base section, the first end portion being provided on a first support body side, in an extending direction of the elongated shaft, of the connection base section, the first protrusion section and the second protrusion section support the first support body rotatably about the second shaft, the connection base section receives insertion of a connection section of the elongated shaft from a second end portion of the connection base section opposed to the first end portion of the connection base section in the extending direction of the elongated shaft, and the first end portion of the connection base section includes a partition with a communication hole passing through the partition in the extending direction of the elongated shaft.

10. The robotic surgical instrument according to claim 9, further comprising:

a seal member that seals the communication hole, wherein the seal member includes an insertion hole through which the wire of the elongated element is configured to be inserted.

11. The robotic surgical instrument according to claim 10, wherein the seal member includes a slit that is configured to guide the wire to the insertion hole.

12. The robotic surgical instrument according to claim 10, wherein the seal member is compressed between the partition and the connection section.

13. The robotic surgical instrument according to claim 10, wherein the seal member is a silicone seal.

14. The robotic surgical instrument according to claim 1, wherein the end effector includes one or two end effector members.

15. A robotic surgical system, comprising:

a robot arm; and a robotic surgical instrument that is detachably attached to the robot arm, wherein the robotic surgical instrument includes an end effector, a first support body that supports the end effector rotatably about a first shaft, a second support body that supports the first support body rotatably about a second shaft, an elongated element to rotate the first support body with respect to the second support body, an elongated shaft to which the second support body is connected, and a housing that is configured to be attached to the robot arm, the elongated element includes a wire, two protection tubes fixed to the wire, and an attachment fixed to a middle of the wire between the two protection tubes, the first support body includes: a pulley section that is rotatably supported by the second shaft and formed with a pulley groove to which the elongated element is configured to be partially wound; a recess that is recessed from the pulley groove in the first support body and to which the attachment is configured to be fitted; and a through-hole extending through the first support body at a position shifted from the recess and having a size through which the attachment and the two protection tubes are passable, the through-hole is connected to the recess via a communication passage that connects a middle portion of the through-hole in a direction of a length of the through-hole and the recess in the first support body such that when the attachment of the elongated element is inserted in the through-hole, the attachment is movable from the through-hole through the communication passage to the recess so as to be engaged with the recess, and the communication passage comprises a second through-hole extending through the first support body in a direction orthogonal to the length of the through-hole.

16. A method of assembling a robotic surgical instrument, comprising:

preparing an assembly, which includes an end effector, a first support body that supports the end effector rotatably about a first shaft, and a second support body that supports the first support body rotatably about a second shaft, wherein the first support body includes: a pulley section that is rotatably supported by the second shaft and formed with a pulley groove; a recess that is recessed from the pulley groove in the first support body; and a through-hole extending through the first support body at a position shifted from the recess and connected to the recess via a communication passage that connects a middle portion of the through-hole in a direction of a length of the through-hole and the recess, wherein the communication passage comprises a second through-hole extending through the first support body in a direction orthogonal to the length of the through-hole;

preparing an elongated element in which an attachment and two protection tubes are fixed to a wire, wherein the attachment is fixed at a middle of the wire between the two protection tubes;

inserting the elongated element in which the attachment and the two protection tubes are fixed to the wire into the through-hole of the first support body of the assembly having a size through which the attachment and the two protection tubes are passable, so as to pass one of the two protection tubes though the through-hole and have the attachment of the elongated element inserted in the through-hole; and drawing the elongated element to move the attachment of the elongated element from the through-hole to the recess through the communication passage, so as to engage the attachment with the recess.

17. The method of assembling a robotic surgical instrument according to claim 16, further comprising:

inserting the wire through an insertion hole of a seal member; and sealing an inner space of the second support body with the seal member having the wire inserted through the insertion hole of the seal member.

* * * * *